(12) United States Patent
Anders et al.

(10) Patent No.: US 7,695,504 B2
(45) Date of Patent: *Apr. 13, 2010

(54) METHOD FOR REGENERATION AND FUNCTIONAL RECOVERY AFTER SPINAL CORD INJURY USING PHOTOTHERAPY

(75) Inventors: Juanita J. Anders, Potomac, MD (US); Ilko K. Ilev, Rockville, MD (US); Ronald W. Waynant, Clarksville, MD (US); Kimberly R. Byrnes, Gaithersburg, MD (US)

(73) Assignees: The United States of America as represented by the Department of Health and Human Services, Washington, DC (US); Henry M. Jackson Foundation for the Advancement of Military Medicine, Rockville, MD (US)

(*) Notice: Subject to any disclaimer, the term of this patent is extended or adjusted under 35 U.S.C. 154(b) by 76 days.

This patent is subject to a terminal disclaimer.

(21) Appl. No.: 11/970,425

(22) Filed: Jan. 7, 2008

(65) Prior Publication Data

US 2008/0103562 A1 May 1, 2008

Related U.S. Application Data

(63) Continuation of application No. 11/022,314, filed on Dec. 23, 2004, now Pat. No. 7,344,555, which is a continuation-in-part of application No. 10/820,443, filed on Apr. 7, 2004, now abandoned.

(60) Provisional application No. 60/460,421, filed on Apr. 7, 2003.

(51) Int. Cl.
*A61N 5/06* (2006.01)
(52) U.S. Cl. .......................................... 607/88; 128/898
(58) Field of Classification Search ................ 607/117, 607/43, 88–94; 606/2–19, 246, 279; 128/898
See application file for complete search history.

(56) References Cited

U.S. PATENT DOCUMENTS

| | | | |
|---|---|---|---|
| 3,375,755 A | 5/1973 | Eggleton et al. | |
| 3,810,367 A | 5/1974 | Peterson | |
| 4,315,514 A | 2/1982 | Drewes et al. | |
| 4,343,301 A | 8/1982 | Indech | |
| 4,630,273 A | 12/1986 | Inoue et al. | |
| 4,633,872 A | 1/1987 | Chaffee et al. | |
| 4,669,466 A | 6/1987 | L'Esperance | |
| 4,671,285 A | 6/1987 | Walker | |
| 4,798,215 A | 1/1989 | Turner | |
| 4,846,196 A | 7/1989 | Wiksell et al. | |
| 4,930,504 A | 6/1990 | Diamantopolous et al. | |
| 4,951,482 A | 8/1990 | Gilbert | |
| 4,951,653 A | 8/1990 | Fry et al. | |
| 4,966,144 A | 10/1990 | Rochkind et al. | |
| 5,029,581 A | 7/1991 | Kaga et al. | |
| 5,037,374 A | 8/1991 | Carol | |
| 5,047,006 A * | 9/1991 | Brandston et al. ............. 600/21 |
| 5,054,470 A | 10/1991 | Fry et al. | |
| 5,150,704 A | 9/1992 | Tatebayashi et al. | |
| 5,259,380 A | 11/1993 | Mendes et al. | |
| 5,267,294 A | 11/1993 | Kuroda et al. | |
| 5,282,797 A | 2/1994 | Chess | |
| 5,358,503 A | 10/1994 | Bertwell et al. | |
| 5,401,270 A | 3/1995 | Muller et al. | |
| 5,441,495 A | 8/1995 | Liboff et al. | |
| 5,445,146 A * | 8/1995 | Bellinger ..................... 607/89 |
| 5,445,608 A | 8/1995 | Chen et al. | |
| 5,464,436 A | 11/1995 | Smith | |
| 5,501,655 A | 3/1996 | Rolt et al. | |
| 5,511,563 A | 4/1996 | Diamond | |
| 5,540,737 A | 7/1996 | Fenn | |
| 5,580,550 A | 12/1996 | Gough et al. | |
| 5,580,555 A | 12/1996 | Schwartz | |
| 5,601,526 A | 2/1997 | Chapelon et al. | |
| 5,616,140 A | 4/1997 | Prescott | |
| 5,621,091 A | 4/1997 | Kunkel et al. | |
| 5,622,168 A | 4/1997 | Keusch et al. | |
| 5,627,870 A | 5/1997 | Kopecky | |
| 5,640,978 A * | 6/1997 | Wong ........................ 128/898 |

(Continued)

FOREIGN PATENT DOCUMENTS

DE 32 00 584 A1 7/1983

(Continued)

OTHER PUBLICATIONS

Van Breugel, H.H.F.I., Bar, P.R., "He-Ne Laser Irradiation Affects Profileration of Cultered Rat Schwann Cells in Dose-dependent Manner", 1993, Journal of Neurocytology, 22, 185-190.*

(Continued)

*Primary Examiner*—Henry M Johnson, III
*Assistant Examiner*—Aisha Hunte
(74) *Attorney, Agent, or Firm*—Knobbe, Martens, Olson & Bear, LLP

(57) ABSTRACT

A method of treating spinal cord injury (SCI) includes transcutaneously irradiating at least a portion of a spinal environment of the patient with light having a power density of at least about 0.01 mW/cm$^2$ at the portion of the spinal environment.

9 Claims, 24 Drawing Sheets

U.S. PATENT DOCUMENTS

| | | | |
|---|---|---|---|
| 5,643,334 | A | 7/1997 | Eckhouse et al. |
| 5,728,090 | A | 3/1998 | Martin et al. |
| 5,748,845 | A * | 5/1998 | Labun et al. .................. 706/10 |
| 5,755,752 | A | 5/1998 | Segal |
| 5,817,008 | A | 10/1998 | Rafert et al. |
| 5,842,477 | A | 12/1998 | Naughton et al. |
| 5,843,073 | A | 12/1998 | Sinofsky |
| 5,879,376 | A | 3/1999 | Miller |
| 5,902,741 | A | 5/1999 | Purchio et al. |
| 5,928,207 | A | 7/1999 | Pisano et al. |
| 5,928,945 | A | 7/1999 | Seliktar et al. |
| 5,954,762 | A | 9/1999 | Di Mino et al. |
| 5,983,141 | A | 11/1999 | Sluijter et al. |
| 5,989,245 | A | 11/1999 | Prescott |
| 6,033,431 | A | 3/2000 | Segal |
| 6,042,531 | A | 3/2000 | Holcomb |
| 6,045,575 | A | 4/2000 | Rosen et al. |
| 6,046,046 | A | 4/2000 | Hassanein |
| 6,060,306 | A | 5/2000 | Flatt et al. |
| 6,063,108 | A | 5/2000 | Salansky et al. |
| 6,074,411 | A * | 6/2000 | Lai et al. ...................... 607/89 |
| 6,107,325 | A | 8/2000 | Chan et al. |
| 6,107,608 | A | 8/2000 | Hayes |
| 6,112,110 | A | 8/2000 | Wilk |
| 6,117,128 | A | 9/2000 | Gregory |
| 6,129,748 | A | 10/2000 | Kamei |
| 6,143,878 | A | 11/2000 | Koopman et al. |
| 6,146,410 | A | 11/2000 | Nagypal et al. |
| 6,149,679 | A | 11/2000 | Di Mino et al. |
| 6,156,028 | A | 12/2000 | Prescott |
| 6,171,239 | B1 * | 1/2001 | Humphrey ................. 600/372 |
| 6,179,771 | B1 | 1/2001 | Mueller |
| 6,187,210 | B1 | 2/2001 | Lebouitz et al. |
| 6,198,958 | B1 | 3/2001 | Ives et al. |
| 6,210,317 | B1 | 4/2001 | Bonlie |
| 6,214,035 | B1 | 4/2001 | Streeter |
| 6,221,095 | B1 | 4/2001 | Van Zuylen et al. |
| 6,223,071 | B1 * | 4/2001 | Lundahl et al. ............ 600/476 |
| 6,233,480 | B1 * | 5/2001 | Hochman et al. .......... 600/476 |
| 6,267,780 | B1 | 7/2001 | Streeter |
| 6,273,905 | B1 * | 8/2001 | Streeter ....................... 607/89 |
| 6,277,974 | B1 | 8/2001 | Lo et al. |
| 6,290,713 | B1 | 9/2001 | Russell |
| 6,290,714 | B1 | 9/2001 | Streeter |
| 6,312,451 | B1 | 11/2001 | Streeter |
| 6,344,050 | B1 | 2/2002 | Chen |
| 6,358,272 | B1 | 3/2002 | Wilden |
| 6,363,285 | B1 | 3/2002 | Wey |
| 6,364,907 | B1 | 4/2002 | Obochi et al. |
| 6,379,295 | B1 | 4/2002 | Woo |
| 6,395,016 | B1 | 5/2002 | Oron et al. |
| 6,397,107 | B1 | 5/2002 | Lee et al. |
| 6,402,678 | B1 | 6/2002 | Fischell et al. |
| 6,421,562 | B1 | 7/2002 | Ross |
| 6,443,974 | B1 | 9/2002 | Oron et al. |
| 6,443,978 | B1 * | 9/2002 | Zharov ....................... 607/91 |
| 6,471,716 | B1 | 10/2002 | Pecukonis |
| 6,514,220 | B2 | 2/2003 | Melton, Jr. et al. |
| 6,537,304 | B1 | 3/2003 | Oron |
| 6,551,308 | B1 | 4/2003 | Muller et al. |
| 6,663,659 | B2 | 12/2003 | McDaniel et al. |
| 6,921,413 | B2 * | 7/2005 | Mahadevan-Jansen et al. .......................... 607/89 |
| 7,303,578 | B2 | 12/2007 | De Taboada et al. |
| 7,344,555 | B2 | 3/2008 | Anders et al. |
| 2001/0044623 | A1 | 11/2001 | Chen |
| 2002/0029071 | A1 * | 3/2002 | Whitehurst .................. 607/88 |
| 2002/0068927 | A1 | 6/2002 | Prescott |
| 2002/0087205 | A1 | 7/2002 | Chen |
| 2002/0099295 | A1 * | 7/2002 | Gil et al. ..................... 600/476 |
| 2002/0123781 | A1 | 9/2002 | Shanks et al. |
| 2002/0188334 | A1 | 12/2002 | Carlgren |
| 2002/0198575 | A1 | 12/2002 | Sullivan |
| 2003/0125782 | A1 | 7/2003 | Streeter |
| 2003/0130709 | A1 * | 7/2003 | D.C. et al. ................... 607/88 |
| 2003/0144712 | A1 | 7/2003 | Streeter |
| 2003/0167080 | A1 | 9/2003 | Hart et al. |
| 2003/0212442 | A1 | 11/2003 | Streeter |
| 2003/0216797 | A1 | 11/2003 | Oron |
| 2004/0014199 | A1 | 1/2004 | Streeter |
| 2004/0044384 | A1 | 3/2004 | Leber et al. |
| 2004/0132002 | A1 | 7/2004 | Streeter |
| 2004/0153130 | A1 | 8/2004 | Oron |
| 2004/0158300 | A1 * | 8/2004 | Gardiner ..................... 607/88 |
| 2004/0220513 | A1 | 11/2004 | Streeter |
| 2004/0260367 | A1 | 12/2004 | De Taboada et al. |
| 2005/0009161 | A1 | 1/2005 | Streeter |
| 2005/0107851 | A1 | 5/2005 | De Taboada et al. |
| 2005/0159793 | A1 | 7/2005 | Streeter |
| 2006/0167564 | A1 * | 7/2006 | Flaherty et al. ............. 623/57 |

FOREIGN PATENT DOCUMENTS

| | | | |
|---|---|---|---|
| DE | 41 08 328 | A1 | 9/1992 |
| DE | 42 13 053 | A1 | 10/1993 |
| DE | 295 15 096 | U1 | 1/1996 |
| EP | 0 130 950 | | 11/1990 |
| EP | 0 763 371 | | 3/1997 |
| EP | 0 783 904 | A2 | 7/1997 |
| EP | 1 226 787 | A2 | 7/2002 |
| JP | 04023634 | | 2/1992 |
| WO | WO 96/36396 | | 11/1996 |
| WO | WO 98/04321 | | 2/1998 |
| WO | WO 98/22573 | | 5/1998 |
| WO | WO 99/42178 | | 8/1999 |
| WO | WO 99/62599 | A1 | 12/1999 |
| WO | WO 00/35534 | A1 | 6/2000 |
| WO | WO 03/042376 | A1 | 5/2003 |
| WO | WO 03/060399 | A1 | 7/2003 |
| WO | WO 2005/025672 | A1 | 3/2005 |
| WO | WO 2005/092440 | A1 | 10/2005 |

OTHER PUBLICATIONS

Rochkind S., Central Nervous System Transplantation Benefitted by Low-power Laser Irradiation, 1992, Lasers in Medical Science, 7, 143-151.*

Agov, B.S., et al., On the mechanism of therapeutic action of helium-neon laser in ischemic heart disease, *Klin Med (Mosc)*, 1985, pp. 102-105 (Abstract only).

Anders, et al., "Low power laser irradiation alters the rate of regeneration of the rat facial nerve," *Laser Surg. Med.*, 13:72-82 (1993).

Arvidsson, Andreas, et al., Neuronal replacement from endogenous precursors in the adult rat brain after stroke, *Nature Medicine*, vol. 8, No. 9, Sep. 2002, pp. 963-970.

Bartholdi, D. et al., "Expression of pro-inflammatory cytokine and chemokine mRNA upon experimental spinal cord injury in mouse: an in-situ hybridization study," *Eur. J. Neurosci.*, 9:1422-1438 (1997).

Beneviste, E.N., "Inflammatory cytokines within the central nervous system: sources, function, and mechanism of action," *Am. J. Physiol.*, 263:C1-C16 (1992).

Brazzle, John, et al., Active Microneedles with Integrated Functionality, *Technical Digest of the 2000 Solid-State Sensor and Actuator Workshop*, Department of Bioengineering, University of Utah, Salt Lake City, Utah 84112 (five pages) (2000).

Bregman, B.S., "*Recovery of function after spinal cord injury: transplantation strategies*," in *Functional Neural Transplantation*, eds. Dunnet & Björklund, Raven Press, New York, p. 489-529 (1993).

Brill, G.E., et al., *Modifiing influence of low level laser irradiation on the relationships in endothelial cell—blood platelet system*, 10th Congress of the European Society for Photobiology, Vienna, Austria (one page), Jun. 8, 2004.

Brosamle, C., et al., "Cells of origin, course, and termination patterns of the ventral, uncrossed component of the mature rat corticospinal tract," *J. Comp. Neurol.*, 386:293-303 (1997).

Byrnes, K.R., et al., Light Therapy Promotes Axonal Regeneration After Acute Spinal Cord Injury in Adult Rats, Program No. 275.2, *Society for Neuroscience*, 2003, Abstract.

Byrnes, et al., Low Power Laser Irradiation Promotes Axonal Growth in an Animal Model of Acute Spinal Cord Injury, *Society for Neuroscience Abstracts*, No. 114.11, 2000.

Carlson, S.L., et al., "Acute inflammatory response in spinal cord following impact injury," *Exp. Neurol.*, 151:77-88 (1998).

Dirnagl, Ulrich, et al., Pathobiology of ischaemic stroke: an integrated view, *TINS*, vol. 22, No. 9, 1999, pp. 391-397.

Dusart, I., et al., "Secondary cell death and the inflammatory reaction after dorsal hemisection of the rat spinal cord," *Eur. J. Neurosci.*, 6:712-724 (1994).

Eells, J.T., et al., Therapeutic photobiomodulation for methanol-induced retinal toxicity, *Proceedings National Academy of Science (PNAS)*, vol. 100, No. 6, Mar. 18, 2003, pp. 3439-3444.

Elimadi, Aziz, et al., Trimetazidine Counteracts the Hepatic Injury Associated with Ischemia-Reperfusion by Preserving Michondrial Function, *Journal of Pharmacology and Experimental Therapeutics*, vol. 286, No. 1, 1998, pp. 23-28.

Fitch, M.T., et al., "Cellular and Molecular Mechanisms of Glial Scarring and Progressive Cavitation: in Vivo and in Vitro Analysis of Inflammation-Induced Secondary Injury After CNS Trauma," *J. Neurosci.*, 19:8182-8198 (1999).

Funk, J.O., et al., "Cytokine production after helium-neon laser irradiation in cultures of human preipheral blood mononuclear cells," *J. Photochem. Photobiol. B:Biol.*, 16:347-355 (1992).

Gage, Fred H., Brain, Repair Yourself, *Scientific American*, Sep. 2003, pp. 47-53.

Gasparyan, Levon V., et al., *Low Level Laser Therapy of Male Genital Tract Chronic Inflammations*, WALT 2-nd Congress (Kansas City, USA), 1998 (two pages).

Gasparyan, L.V., et al., *The influence of LED irradiation at different wavelengths on functional activity of blood platelets*, 10th Congress of the European Society for Photobiology, Vienna, Austria, 2003 (one page).

Gasparyan, L.V., et al., *The influence of LED irradiation at different wavelengths with antioxidants on functional activity of blood platelets*, Laser, Florence, 2003 (one page).

Gasparyan, Levon V., Biochemical and Biophysical Effects of Low Level Laser Irradiation, *MAL 2000*, Helsinki, Finland (three pages).

Gasparyan, Levon V., Experience of Russian (former USSR) Scientists in LLLT and UV Blood Irradiation, *MAL 2000*, Helsinki, Finland (four pages).

Gasparyan, Levon V., *Investigation of Sensations, Associated with Laser Blood Irradiation*, WALT 2-nd Congress (Kansas City, USA), 1998 (two pages).

Gasparyan, Levon V., Millimeter Wave Therapy, *MAL 2000*, Helsinki, Finland (three pages).

Greco, et al., "Increase in RNA and protein synthesis by mitochondria irradiated with He-Ne laser," *Biochem. Biophys. Res. Commun.*, 163:1428-1434 (1989).

Gross, Garrett J., et al., *Mechanisms of Postischemic Contractile Dysfunction*, Myocardial Protection From Surgical Ischemic-Reperfusion Injury, An International Symposium, Asheville, North Carolina, Sep. 21-24, 1997, pp. 1898-1904.

Hamada, Y., et al., "Involvement of an interdellular adhesion molecule 1-dependent pathway in the pathogenesis of secondary changes after spinal cord injury in rats," *J. Neurochem.*, 66:1525-1531 (1996).

Hammon, John W. Jr., M.D., et al., Myocardial Protection Form Surgical Ischemic-Reperfusion Injury, *Ann. Thorac. Surg.*, 1999:68:1897.

Hamers, F.T.P., et al., "Automated Quantitative Gait Analysis During Overground Locomotion in the Rat: Its Application to Spinal Cord and Transection Injuries," *J. Neurotrauma*, 18:187-201(2001).

Hicks, S.P. et al., "Locating corticospinal neurons by retrograde axonal transport of horseradish peroxidase," *Exp. Neurol.*, 56:410-420 (1977).

Iadecola, Costantino, et al., Inhibition of inducible nitric oxide synthase ameliorates ischemic damage, *Am. J. Physiol.*, 268:R286-R292(1995).

Ilev, I., et al., "Smart optical fiber probes for precise tissue treatment," *Proc. SPIE*, 4616:220-228 (2002).

Kalderon, N., et al., "Structural recovery in lesioned adult mammalian spinal cord by x-irradiation of the lesion site," *Proc. Nat'l. Acad. Sci. USA*, 93:11179-84 (1996).

Kalderon, N., et al., "Severed corticospinal axons recover electrophysiologic control of muscle activity after x-ray therapy in lesioned adult spinal cord," *Proc. Natl. Acad. Sci. USA*, 93:11185-90 (1996).

Karu, Tiina, Mechanisms of Low-Power Laser Light Action on Cellular Level, *Effects of Low-Power Light on Biological Systems V*, Proceedings of SPIE, Jul. 7, 2000, vol. 4159, 2000.

Karu, T.I., *Low power laser therapy*, in Biomedical Photonics Handbook, Ch. 48, Editor-in-Chief Tuan Vo-Dinh, Boca Raton, CRC Press, 2003.

Karu, Tiina, *Mechanisms of interaction of monochromatic visible light with cells*, Proc. SPIE, vol. 2630, pp. 2-9, 1994.

Karu, Tiina, Photobiological Fundamentals of Low Power Laser Therapy, *IEEE Journal of Quantum Electronics*, vol. QE-23, No. 10, Oct. 1987, pp. 1703-1717.

Klusman, I., et al., "Effects of pro-inflammatory cytokines in experimental spinal cord injury," *Brain Res.*, 762:173-184 (1997).

Koshinaga, M., et al., "The temporal and spatial activation of microglia in fiber tracts undergoing anterograde and retrograde degeneration following spinal cord lesion," *J. Neurotrauma*, 12:209-222 (1995).

Kunkel-Bagden, E., et al., "Spinal cord transplants enhance the recovery of locomotor function after spinal cord injury at birth," *Exp. Brain Res.*, vol. 81, 1990, pp. 25-34.

Kunkel-Bagden, E., et al., "Recovery of function after spinal cord hemisection in newborn and adult rats: differential effects on reflex and locomotor function," *Exp. Neurol.*, vol. 116, 1992, pp. 40-51.

Kunkel-Bagden, E et al., "Method to assess the development and recovery of locomotor function after spinal cord injury in rats," *Exp. Neurol.*, 119:153-164 (1993).

*The Laser Exchange: Delivering the medicine of the future*, www.laserexchange.co.uk/laser-therapy/ultrasoun.htm, 42 pages, Oct. 13, 2004.

Lam, T.S., et al., "Laser stimulation of collagen synthesis in human skin fibroblast cultures," *Lasers Life Sci.*, 1:61-77 (1986).

Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Lasers in Surgery and Medicine*, vol. 31, 2002, pp. 283-288.

Metz, G.A., et al., "Cortical and subcortical lesions impair skilled walking in the ladder rung walking test: a new task to evaluate fore- and hind limb stepping, placing, and co-ordination," *J. Neurosci. Methods*, vol. 115, 2002, pp. 169-179.

Minoru, Asahi, et al, *Expression of Interleukin-1 [beta] Converting Enzyme Gene Family and bcl-2 Gene Family in the Rat Brain Following Permanent Occlusion of the Middle Cerebral Artery*, Journal of Cerebral Blood Flow & Metabolism, vol. 17(1), Jan. 1997, pp. 11-18.

Mochizuki-Oda, Noriko, et al., Effects of near-infra-red laser irradiation on adenosine triphosphate and adenosine diphosphate contents of rat brain tissue, *Neuroscience Letters 323*, May 3, 2002, pp. 207-210.

Nash, H.H., et al., "Ensheathing cells and methylprednisolone promote axonal regeneration and functional recovery in the lesioned adult rat spinal cord," *J. Neurosci.*, 22:7111-20 (2002).

Nishioka, Norman S., et al., Reflection and Transmission of Laser Light From the Esophagus: The Influence of Incident Angle, *Gastroenterology*, vol. 94, 1988, pp. 1180-1185.

Olesin, Al, et al., Laser irradiation of venous blood for production of reperfusion syndrome in myocardial infarction, *Patologisheskaia fiziologiia*, 1992 (Abstract only).

Oron, Uri, et al., Attenuation of Infarct Size in Rats and Dogs after Myocardial Infarction by Low-Energy Laser Irradiation, *Lasers in Surgery and Medicine*, vol. 28, 2001, pp. 204-211.

Oron, Uri, et al., Low-Energy Laser Irradiation Reduces Formation of Scar Tissue After Myocardial Infarction in Rats and Dogs, *Circulation*, vol. 103, Jan. 16, 2001, pp. 296-301.

Pan, J.Z., at al., "Cytokine activity contributes to induction of inflammatory cytokine mRNAs in spinal cord following contusion," *Neurosci. Res.*, 68:315-322 (2002).

Park, James L., Ph.D., et al., Mechanisms of Myocardial Reperfusion Injury, *The Annals of Thoracic Surgery*, Official Journal of The Society of Thoracic Surgeons and the Southern Thoracic Surgical Association, vol. 68, No. 5, Nov. 1999, pp. 1905-1912.

Popovich, P.G., et al., "The cellular inflammatory response after spinal cord injury in Sprague-Sawley and Lewis rats," *J. Comp. Neurol.*, vol. 377, 1997, pp. 443-464.

Popovich, P.G., et al., "The neuropathological and behavioral consequences of intraspinal microglial/macrophage activation," *J. Neuropathol. Exp. Neurol.*, 61:623-633 (2002).

Rochkind, et al., New Methods of Treatment of Severely Injured Sciatic Nerve and Spinal Cord, *Acta Neurochirurgica*, vol. 43, pp. 91-93, 1988, abstract.

Saperia, D., et al., "Demonstration of elevated type I and III procollogen mRNA level in cutaneous wounds treated with helium-neon laser: Proposed mechanism for enhanced wound healing," *Biochem. Biophys: Res. Commun.*, 138:1123-1128 (1986).

Semenza, Gregg L., et al., Regulation of Mammalian $O_2$ Homeostasis by Hypoxia-Inducible Factor 1, *Ann. Rev. Cell Dev. Biol.*, vol. 15, 1999, pp. 551-578.

Snyder, S.K., et al., "Quantitation of calcitonin gene-related peptide mRNA and neuronal cell death in facial motor nuclei following axotomy and 633 nm low power laser treatment," *Surg. Med.*, 31:216-222 (2002).

Streeter, J., et al., "Mechanisms of action of light therapy for stroke and acute myocardial infarction," *Mitochondrion* 4:569-576 (2004).

Stys, Peter K., Anoxia and Ischemic Injury of Myelinated Axons in CNS White Matter: From Mechanistic Concepts to Therapeutics, *J. Cereb. Blood Flow Metab.*, 18:2-25 (Jan. 1998).

*Is LLLT Different from Ultrasound?*, http://www.thorlaser.com/LLLT/is-LLLT-diff-from-ultrasound.htm, 2 pages, Oct. 13, 2004.

Product List, Tho, lllt, LLLT, *Low Level Laser Therapy, Laz.*, http://www.thorlaser.com/prodlist/index.html, Oct. 6, 1999, pp. 1-4.

Specifications, Thor, lllt, LLLT , *Low Level Laser Therapy, low level laser therapy*, http://www.thorlaser.com/specs, Oct. 6, 1999, pp. 1-2.

100mW, Thor, lllt, LLLT, *Low Level Laser Therapy, low level laser therapy, Lazer, Thorl.*, http://www.thorlaser.com/_specs/_100m_W.html, Oct. 6, 1999, p. 1.

200mW, Thor, lllt, LLLT, *Low Level Laser Therapy, low level laser therapy, Lazer, Thorl.*, http://www.thorlaser.com/_specs/200m_W.html, Oct. 6, 1999, p. 1.

500mW, Thor, lllt, LLLT, *Low Level Laser Therapy, low level laser therapy, Lazer, Thorl.*, http://www.thorlaser.com/_specs/500m_W.html, Oct. 6, 1999, p. 1.

200mW, Thor, lllt, LLLT, *Low Level Laser Therapy, low level laser therapy, Laser, Thorl.*, http://www.thorlaser.com/_specs/200m_W650nm.html, Oct. 6, 1999, p. 1.

680nm PROBE, Thor, lllt, LLLT, *Low Level Laser Therapy, low level laser therapy, Laser*, http://www.thorlaser.com/_specs/680.html, Oct. 6, 1999, p. 1.

Toon, John, Taking the "Ouch" Out of Needles: Arrays of Micron-Scale "Microneedles" Offer New Technique for Drug Delivery, *Georgia Tech Research News*, Jun. 22, 1998 (three pages).

Toricelli, P., et al., Laser Biostimulation of cartilage: in vitro evaluation, *Biomed Pharmacother* 2001, vol. 55, pp. 117-120.

Tuchin, Valery, *Tissue Optics: Light Scattering Methods and Instruments for Medical Diagnosis*, SPIE Press, Tutorial Texts in Optical Engineering, vol. TT38, 2000, pp. 3-11.

Tunér, Jan, et al., Low Level Laser Therapy, *Clinical Practice and Scientific Background*, Prima Books in Sweden AB, 1999, pp. 1-9, 45-58, 59-109, 62-114; 113-116, 118, 132-134, 134-135; 149-151; 151-156; 185; 334-364.

Van Brugel, Hans H.F.I., et al., *Power Density and Exposure Time of He-Ne Laser Irradiation are More Important than Total Energy Dose in Photo-Biomoducation of Human Fibroblasts in Vitro*, 1992, Wiley-Liss, Inc.

Whelan, H.T., et al., "Effect of NASA Light-Emitting Diode Irradiation on Wound Healing," *J. Clinical Laser Med. & Surg.*, 19:305-314 (2001).

Whishaw, I.Q., et al., "Absence of impairments or recovery mediated by the uncrossed pyramidal tract in the rat versus enduring deficits produced by the crossed pyramidal tract," *Behav. Brain Res.*, vol. 134, 2002, pp. 323-336.

Wong-Riley, Margaret T.T., et al., Light-emitting diode treatment reverses the effect of TTX on cytochrome oxidase in neurons, NeuroReport, *NeuroReport*, vol. 12, No. 14, Oct. 8, 2001, pp. 3033-3037.

Yaakobi, Tali, et al., Long-term effect of low energy laser irradiation on infarction and reperfusion injury in the rate heart, *J. Appl. Physiol.*, vol. 90, 2001, pp. 2411-2419.

Yu, W., et al., "Photomodulation of Oxidative Metabolism and Electron Chain Enzymes in Rat Liver Mitochondria," *Photochem. and Photobio.*, 66:866-871 (1997).

\* cited by examiner

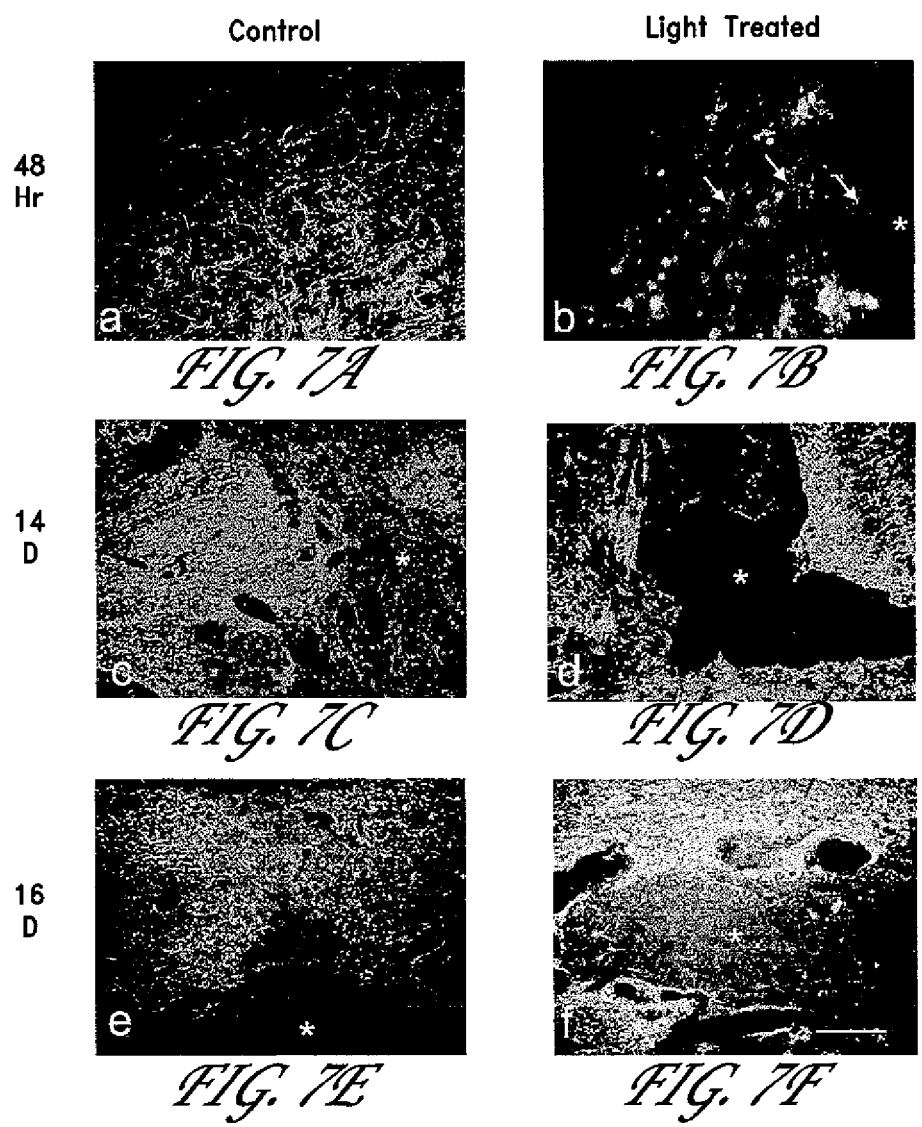
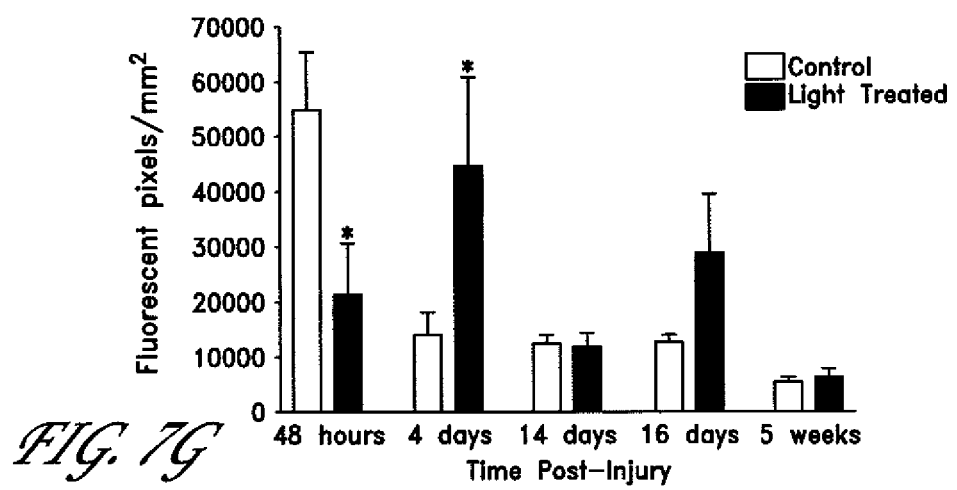

Control　　　　　　　　　Light Treated

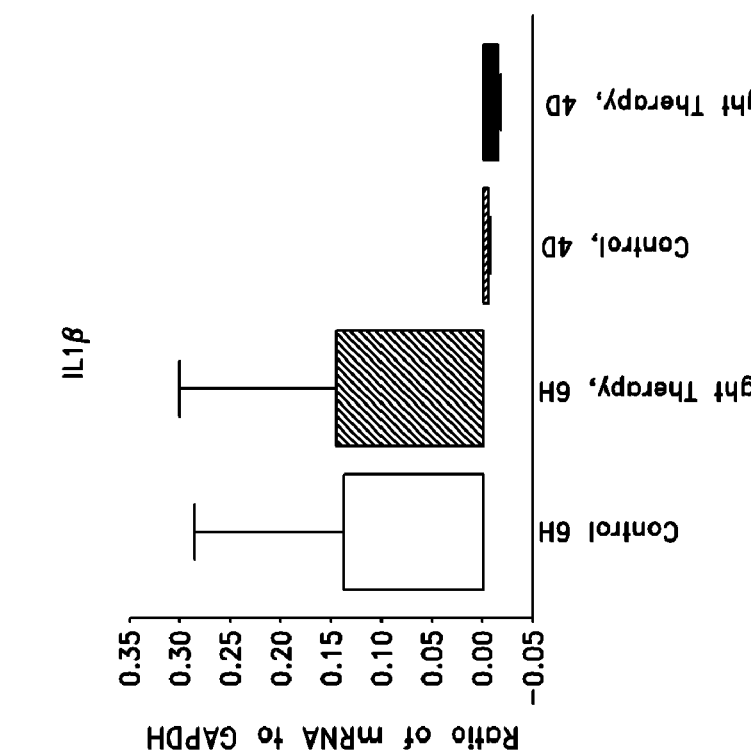
FIG. 10C
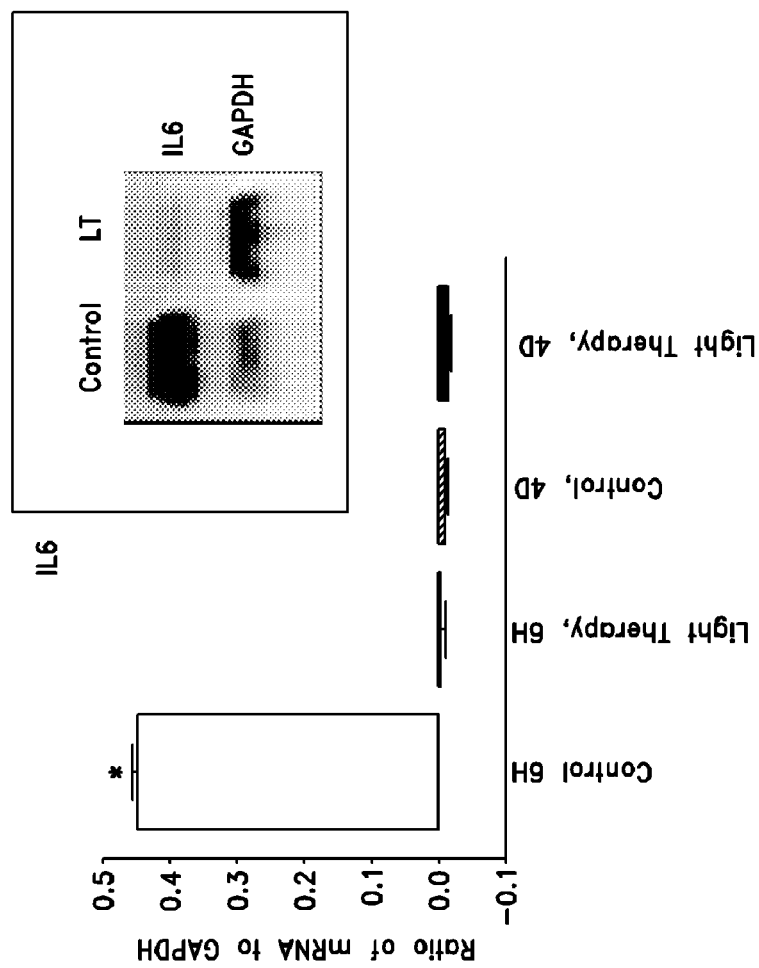
FIG. 10B
FIG. 10A

METHOD FOR REGENERATION AND FUNCTIONAL RECOVERY AFTER SPINAL CORD INJURY USING PHOTOTHERAPY

CLAIM OF PRIORITY

This application is a continuation of U.S. patent application Ser. No. 11/022,314, filed Dec. 23, 2004, now U.S. Pat. No. 7,344,555 which is incorporated in its entirety by reference herein and which is a continuation-in-part of U.S. application Ser. No. 10/820,443, filed Apr. 7, 2004 and now abandoned, which is incorporated in its entirety by reference herein and which claims the benefit of priority under 35 U.S.C. § 119(e) to U.S. Provisional Patent Application No. 60/460,421, filed Apr. 7, 2003, which is incorporated in its entirety by reference herein.

BACKGROUND OF THE INVENTION

Spinal cord injury (SCI) is a serious clinical problem with approximately eight thousands new cases every year. SCI occurs when a traumatic event results in damage to cells within the spinal cord or severs the nerve tracts that relay signals up and down the spinal cord. The most common types of SCI include contusion and compression. Other types of injuries include lacerations, and central cord syndrome (specific damage to the corticospinal tracts of the cervical region of the spinal cord). Severe SCI often causes paralysis and loss of sensation and reflex function below the point of injury, and also autonomic dysfunction affecting breathing, bowel and bladder control, and blood pressure. SCI patients are also prone to develop secondary medical problems, such as bladder infections, pneumonias, and skin ulcers.

Spinal cord damage often results in permanent disability due to the inability of axons within the central nervous system to regenerate following an injury. While recent advances in emergency care and rehabilitation allow many SCI patients to survive, methods for reducing the extent of injury and for restoring function are still limited. Acute treatment for SCI includes techniques to relieve cord compression, prompt (within 8 hours of the injury) drug therapy with corticosteroids such as methylprednisolone to minimize cell damage, and stabilization of the vertebrae of the spine to prevent further injury. Despite vigorous research into the use of inflammatory drugs, ionizing irradiation, elimination of inhibitory factors in the spinal cord, provision of neurotrophic factors, and cell transplantation, there currently is no cure for the neurological deficits seen following SCI.

SUMMARY OF THE INVENTION

The present invention relates generally to the treatment of SCI by stimulating axon regeneration within the central nerve system. One aspect of the present invention provides methods of treating SCI with low power laser irradiation (LPLI). Another aspect of the present invention provides methods of treating SCI by modulating a gene activity to stimulate axon regeneration. In this regard, the present invention also provides compositions that modulate genes expression relating to the neuron regeneration after SCI. Another aspect of the present invention provides methods for evaluating the effectiveness of a treatment for SCI.

In one embodiment, there is provided a method of treating spinal cord injury. The method comprises applying a light source to or about at least a portion of a spinal environment, wherein the light source has a wavelength of about 580 nm to about 850 nm, achieving a light density of at least about 0.01 mW/cm$^2$ at the portion of spinal environment, and modulating physiological activity with respect to the spinal environment using the light source. In preferred embodiments, the light source is positioned about 50 cm or less from the portion of the spinal environment. The "spinal environment" comprises a spinal cord, spinal vasculature and the meninges and the cerebrospinal fluid overlying the spinal cord. In preferred embodiments, the physiological activity of the modulating step comprises facilitating axonal regeneration, reducing Wallerian degeneration, and/or modulating one or more physiological activities selected from the group consisting of immunological activity, gene expression, Schwann cell activity, the blood-brain barrier, neovascularization, astroglial scar formation, and growth factor production with respect to the spinal cord.

In another embodiment, there is provided a method of treating spinal cord injury comprising applying a first light source to a first portion of a skin surface overlying at least a portion of a spinal environment, wherein the light source has a wavelength of about 580 nm to about 850 nm, wherein the light source and the first portion of the skin surface form a vector that generally intersects at least a portion of the spinal environment, achieving a light density of at least about 0.1 mW/cm$^2$ at the portion of the skin surface, and maintaining the first light source to the portion of the skin surface generally for a first specified treatment period. In a preferred embodiment, the method further comprises applying a second light source having a wavelength of about 580 nm to about 850 nm to a second portion of the skin surface overlying the central nervous system of a mammal, and terminating the second light source after a second specified treatment period. The second portion of skin surface in the second applying step preferably overlies at least a portion of the motor cortex of the brain or at least a portion of the spinal cord caudal to the site of spinal cord injury.

The methods preferably utilize light having a wavelength in the range of about 580 nm to about 850 nm, including from about 720 nm to about 820 nm, and about 810 nm. The light source may be laser, including diode laser, LED, or other suitable source, and in certain embodiments, preferably has a source power in the range of about 12.5 mW to about 50 W.

In accordance with another embodiment, there is provided a method for treating spinal cord injury, comprising delivering an neuroregenerative effective amount of light energy to a target area of the spinal cord that includes an area of neural injury, wherein delivering the neuroregenerative effective amount of light energy comprises delivering a power density of at least about 0.01 mW/cm$^2$ to the target area of the spinal cord. In a preferred embodiment, delivering a neuroregenerative effective amount of light energy to the target area of the spinal cord comprises determining a surface power density of the light energy sufficient to deliver a predetermined power density of light energy to the target area of the spinal cord of at least about 0.01 mW/cm$^2$.

In accordance with yet another embodiment, there is provided a method for assessing treatment of traumatic spinal cord injury comprising accessing the spinal cord environment of a traumatic spinal cord injury patient, obtaining a first sample of at least a portion of the spinal cord environment, evaluating at least one marker of traumatic spinal cord injury in the first sample; and treating the spinal cord injury patient. The steps of the method may be performed in the recited order or they may be performed in another order. In one embodiment, the method further comprises reaccessing the spinal cord environment of a spinal cord injury patient, obtaining a second sample of at least a portion of the spinal cord environment, and evaluating at least one marker of traumatic spinal cord injury in the second sample. Accessing may be performed by lumbar puncture, and the samples may comprise cerebrospinal fluid or tissue from a needle biopsy. In one embodiment, the method further comprises comparing at least one marker from the first sample to at least one marker from the second sample.

Several embodiments of the invention provide these advantages, along with others that will be further understood and appreciated by reference to the written disclosure, figures, and claims included herein.

BRIEF DESCRIPTION OF THE DRAWINGS

The structure and method of making the invention will be better understood with the following detailed description of embodiments of the invention, along with the accompanying illustrations, in which:

FIG. 7. Immunohistochemistry of astrocytes. Images of control tissue and light treated tissue with antibody against GFAP (glial fibrillary acidic protein) at 48 hours, 14 dpi and 16 dpi. a) Control tissue and b) light treated tissue at 48 hours. Heavy GFAP positive labeling demarcated the lesion in all control tissue, but only light banding near the lesion edge in light treated tissue. c) Control tissue and d) light treated tissue at 14 dpi. *$p<0.05$ between tissues at 48 hours and 14 dpi. e) Control tissue and f) light treated tissue at 16 dpi. *$p<0.05$ between control and light treated tissue. g) GFAP fluorescence between control tissue and light treated tissue at 48 hours, 4 dpi, 14 dpi, 16 dpi and 5 weeks. *$p<0.05$ between control and light treated tissues.

DETAILED DESCRIPTION OF THE PREFERRED EMBODIMENT

Figure 1A:
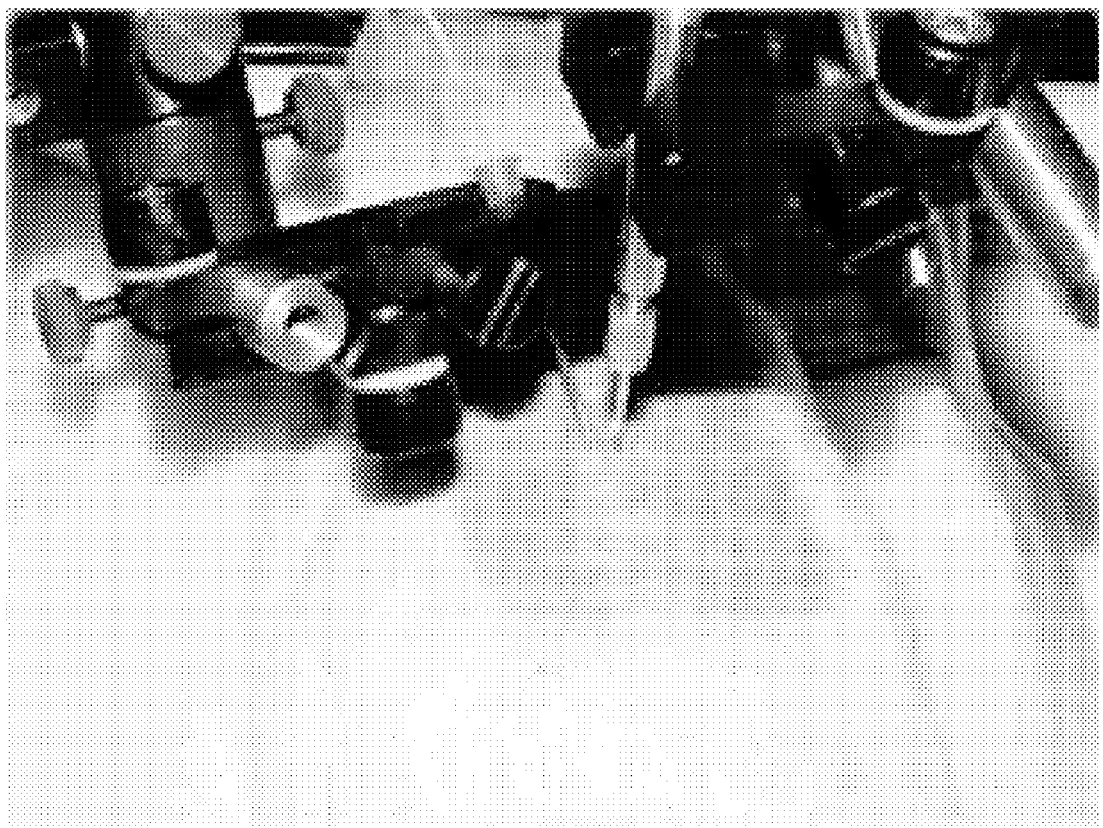
FIG. 1. a) Photograph of spectrophotometric analysis experimental set-up. A smart fiber (arrow) is inserted below the skin of the rat, the light source (arrowhead) is positioned above the skin for transcutaneous application of light. b) Graphical representation of transmission (in arbitrary units) through each layer of tissue, depending on wavelength (nm). Layer 1=skin, 2=loose connective tissue, 3=dense connective tissue, 4=muscle, 5=vertebral column and spinal cord. The graph demonstrates that wavelengths in the 770-810 nm range had the greatest transmission, or penetration, through all levels. c) Human spinal section transmission/scatter measurements. Sampling fiber diameter is 1 mm.

Although axons have the ability to regrow following injury, the spinal cord environmental factors may affect this regrowth. Studies of spinal cord injury (SCI) patients suggest that secondary immunological and vascular effects of SCI cause a greater impairment to recovery than the primary insult to the spinal cord. [Fitch, et al. *J. Neurosci.*, 19:8182-8198 (1999), Dusart and Schwab, *Eur. J. Neurosci.*, 6:712-724 (1994), Koshinaga and Whittemore, *J. Neurotrauma*, 12:209-222 (1995), and Popovich, et al., *J. Neuropathol. Exp. Neurol.*, 61:623-633 (2002)] Researchers have investigated the invasion and activation of immune cells as a potential mediator of secondary injury, including neutrophils, macrophages, microglia, astrocytes and T and B lymphocytes [Dusart and Schwab, *Eur. J. Neurosci.*, 6:712-724 (1994), **]. These cells are primarily activated or drawn into the lesion area by pro-inflammatory cytokines and chemokines expressed following injury [Barholdi and Schwab, *Eur. J. Neurosci.*, 9:1422-1438 (1997), Beneviste, *Am. J. Physiol.* 263:C1-C16 (1992), Klusman and Schwab, *Brain Res.*, 762:173-184 (1997), Pan, et al., *Neurosci. Res.*, 68:315-322 (2002)]. Recent evidence suggests that alteration of cell invasion and activation after SCI may improve functional recovery of spinal cord patients. Vascular effects from breakdown of the blood-brain-barrier (BBB), cytotoxic swelling, hemorrhage and neovascularization may also play a role in the recovery of spinal cord patients. Other secondary phenomena include calcium-, free radical-, nitric oxide- and glutamate-mediated cell injury. It is not known whether the neuronal and axonal changes that occur with SCI, such as demyelination, Schwannosis and Wallerian degeneration, are primary or secondary to these pathological processes.

Light therapy (LT), also known as photo-biomodulation or low power laser irradiation (LPLI), is a non-invasive treatment which evokes biological effects via the absorption of light. LPLI has been shown to increase neuronal survival and regeneration in the peripheral nervous system [Anders, et al., *Surg. Med,* 13:72-82 (1993), Snyder, et al., *Surg. Med,* 31:216-222 (2002)]. Investigation has shown that LT, through the absorption of light by a cellular photoreceptor, rather than a heating effect on the cell [Anders, et al., *Surg. Med.* 13:72-82, (1993), and Mochizuki-Oda, et al., *Neurosci. Lett.* 323: 207-210 (2002)]; can modulate ATP, DNA, RNA and protein synthesis, depending on the treatment parameters applied [Saperia, et al., *Biochem. Biophys: Res. Commun.* 138:1123-1128 (1986); Greco, et al., *Biochem. Biophys. Res. Commun.* 163:1428-1434 (1989); Lam, et al., *Lasers Life Sci.* 1:61-77 (1986); Funk, et al., *J. Photochem. Photobiol. B:BBiol.* 16:347-355 (1992); Mochizuki-Oda, et al., Supra (2002)]. Unlike treatment of acute SCI with corticosteroids, LPLI is not associated with side effects of increased infection risk and/or glucose intolerance.

LT research, however, is not extensive within the area of central nervous system (CNS) injury and no study to date has assessed the ability of light to regenerate specific tracts within the spinal cord or determined the recovery of specific locomotor functions. Although the exact mechanism of how LT causes change in the spinal cord is unknown, LT may act through modulation of mitochondrial activity by absorption of light by components of the electron transport chain, alteration in reactive oxygen species production, or through modulation of any of the processes mentioned previously.

Although progress has been made in recent years in the treatment of SCI, there exists a need to develop new treatment for SCI, to improve the efficiency of the existing methods such as LT, and to develop methods to better evaluate the effectiveness of the new treatment modalities.

One aspect of the present invention relates to treatment of SCI using LPLI. It remains unclear exactly what happens to light as it propagates through human tissues, particularly, when more then one tissue type is involved (e.g., skin, muscle, bone, etc.). The analytical solutions of the problem are quite complex and mostly intractable, or, when simplified, inaccurate. The numerical solutions are oversimplifications, or require unavailable/unreliable data, and produce inaccurate solutions. Early studies of light propagation in animal tissues suggested that more light penetrates the deep tissues than expected from the simple analytical solutions or the numerical solutions using ex-vivo measurements of single tissues; using data from existing literature analyzing the propagation of light through complex/multiple tissue type "samples" produced overly pessimistic results. Empirical studies using cadavers reaffirm the earlier findings with animal tissues.

While the expectation/knowledge that more light gets through than predicted makes non-invasive, transcutaneous delivery of light in the treatment of deep tissue possible, relatively large amounts of energy are still needed at the surface of the skin. Most of the energy at the skin will be absorbed by the tissue between the skin and the target tissue; such absorption will increase the tissue's temperature at a rate proportional to the power density, i.e., the number of photons per unit area per unit time.

The LPLI therapy of the present invention is designed to minimize the required power density at the skin while accounting for the tissue scattering to deliver appropriate "treatment doses" to the target tissue. In one embodiment, the laser light has a wave length of about 580 to about 850 nm. In another embodiment, the laser light has a wave length of about 650 nm to about 850 nm. In still another embodiment, the laser light has a wave length preferably about 770 to about 820 nm, and most preferably at about 810 nm. In one embodiment, the laser light has an output power of about 50 mW to about 50 W. In another embodiment, the laser light with an output power of about 100 mW to about 6 W, and most preferably at about 125 mW to about 5.5 W is applied transcutaneously to a mammal at the site of acute injury to the corticospinal tract (CST) for about 7 to about 21 consecutive days and preferably about 14 days. In one embodiment, light irradiation of the brain is performed in addition to irradiation of the lesion site, preferably the motor cortex. In one embodiment, the irradiation zone of the treatment site is changed during the treatment period. In one embodiment, the irradiation zone is enlarged during the treatment period. In one embodiment, the irradiation zone is periodically enlarged and the treatment dose is increased. In one embodiment, the irradiation zone is moved during treatment. In one embodiment, the treatment zone is periodically moved during treatment along the path of expected axonal regrowth. In one embodiment, treatment is initiated within about 24 hours after injury. In another embodiment, the treatment preferably begins immediately after the injury. As is well understood by one skilled in the art, the light density, output, total daily dosage, and the length of the treatment period may vary depending on the form, severity, and site of the particular SCI. In some uses of LT, increases in specific cellular activities are provided, while in other uses of LT, decreases in particular cellular activities are provided. In still other uses of LT, a combination of inhibitory and promotional effects on cellular activity are provided by LT.

Figure 1B:
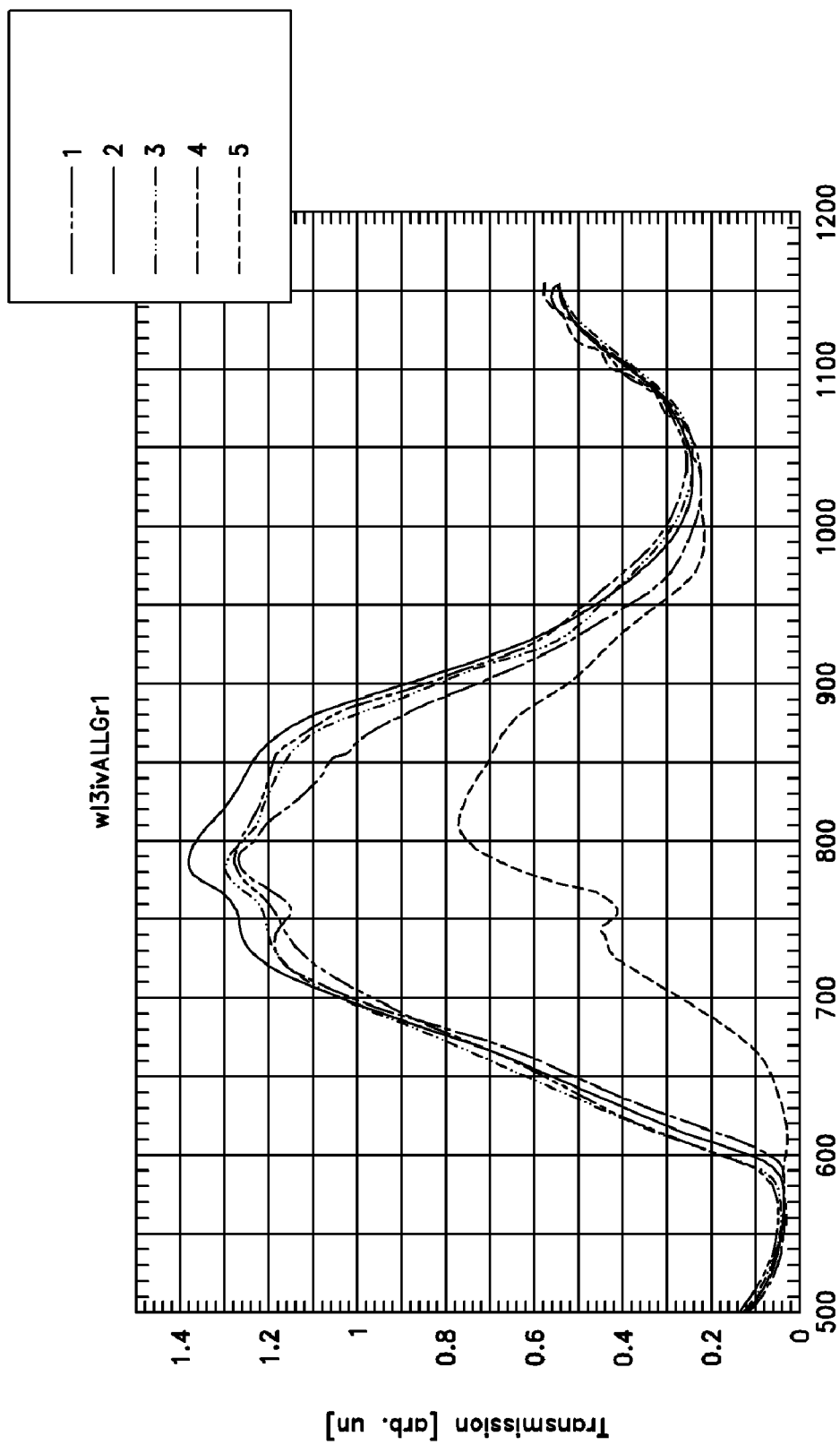
Figure 1C:
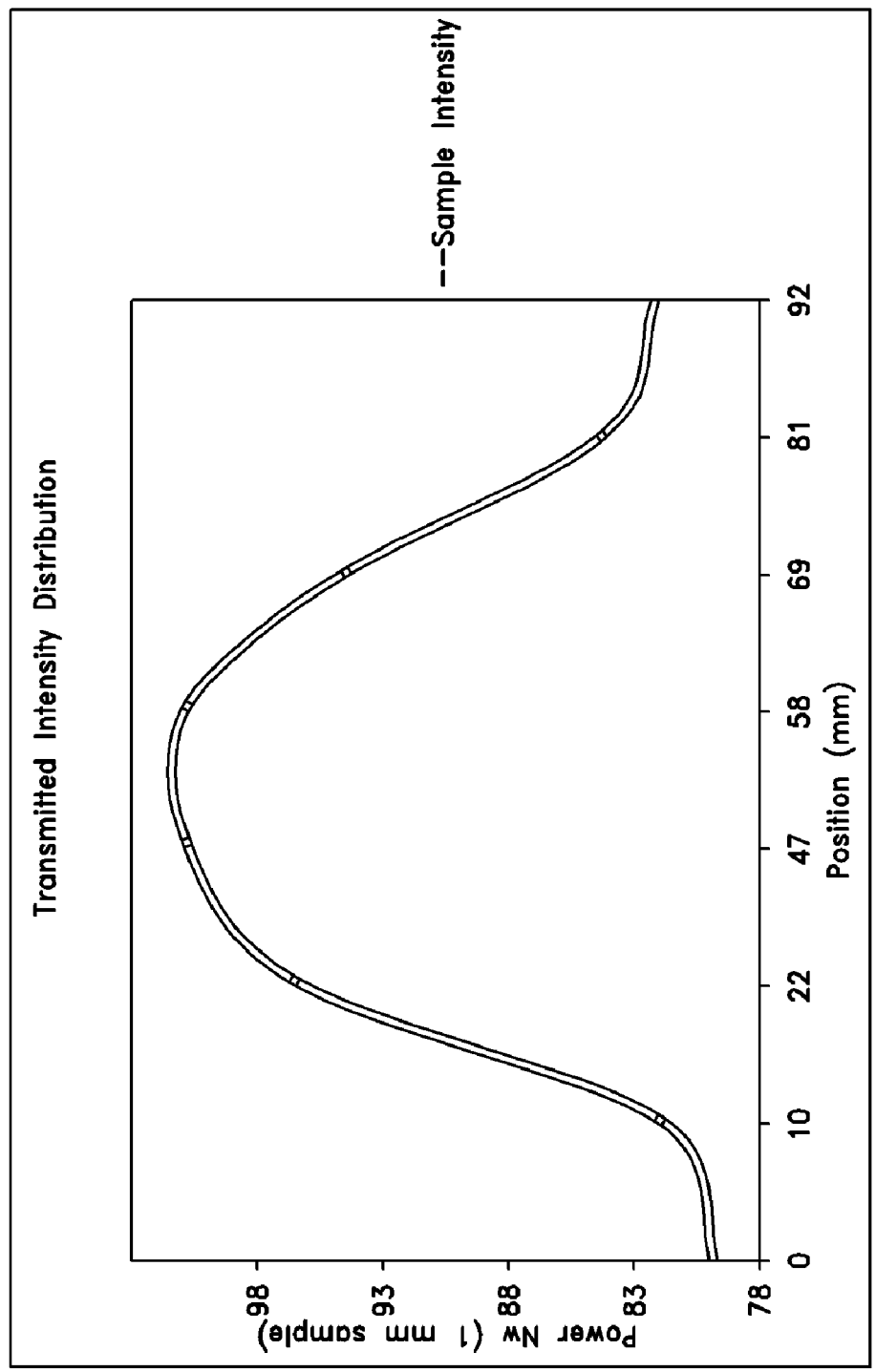

FIG. 1 shows the light transmission through various kinds of tissues between a light source and rat spinal cord. The peak penetration through all tissue layers (i.e., skin, loose connective tissue, dense connective tissue, muscle, and vertebral column) to the spinal cord was found between the 770 nm and 810 nm wavelengths (FIG. 1b). FIG. 1c shows the transmitted light intensity distribution in a human spinal section. The transmission measurements are described in Table 1.

In another embodiment, injured rat spinal cord is transcutaneously irradiated at the lesion site for a total of 14 days with an 810 nm diode laser (Thor International, UK) with 150 mW output through a delivery fiber optic (2,997 seconds treatment time/day). The daily dosage was 1589 J/cm$^2$ (irradiance = 0.53 W/cm$^2$, 450 J).

As shown in FIG. 2, anterograde mini-ruby analysis reveals that the average number of mini-ruby labeled axons in the light treated group was significantly greater than that of the control group ($p<0.0001$, one way ANOVA (analysis of variance) with Tukey post-test; FIG. 2a), with an average of 199.2+/−12.46 labeled axons caudal to the lesion. The mini-ruby labeled axons in the light treated group extended an average of 8.7 +/−0.75 mm caudal to the lesion, significantly longer than the control group ($p<0.01$, one way ANOVA with Tukey post-test; FIG. 2b). The maximum distance traveled over 5 weeks in the light treated group was 14 mm caudal to the lesion, which was reached by 8% of the counted axons (FIG. 2e).

In another preferred embodiment, the effectiveness of the LPLI treatment is confirmed by a double-label, retrograde tracing analysis. At the time of CST lesion, transected neurons are labeled by an anterograde tracer, hydroxystilbamidine methanesulfonate (HM); inserted into the lesion. Ten weeks after CST lesion, axons terminating at vertebral level L3, approximately 24 mm caudal to the initial lesion, are labeled by injection of fast blue into the ventral horn. Numbers of single (HM or fast blue) and double (neurons with axons that are transected and regrew to L3) labeled neurons in the motor cortex are assessed using unbiased stereology.

Figure 3A:
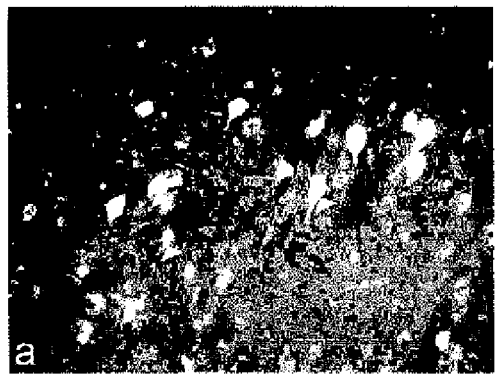
FIG. 3. Photomicrographs of single and double labeled neurons at 10 weeks post-injury. a) Numbers of HM (hydroxystilbamidine methanesulfonate) labeled neurons (arrowheads) in the motor cortex, b) fast blue labeled neurons in the injection site at L3, and c) fast blue labeled neurons in the motor cortex were similar in both groups. d) Graphical representation of comparison of double labeled neurons between light treated and control groups. *$p<0.05$ using Mann Whitney U. Bars represent mean percentage of counted neurons +/−SEM. e-g) Double labeled neurons were found only in motor cortex of light treated rats. Arrows indicate double labeled neurons, identifiable by green punctate label in blue cytoplasm, which is consistent with labeling pattern previously described. [Pyner et al., *Neuroscience* 100:549-556 (2000)]. Bar=67 μm (a-e); 34 μm (f-g).
Figure 3B:
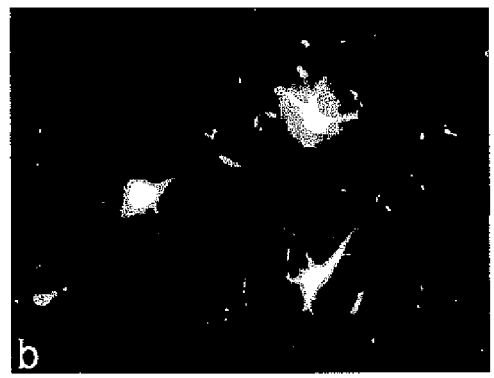
Figure 3C:
Figure 3D:
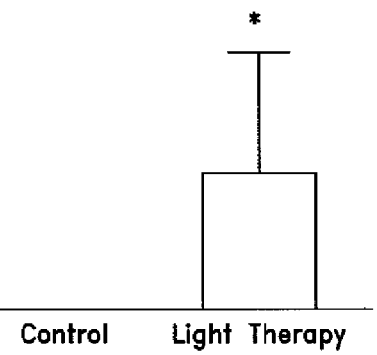
Figure 3E:
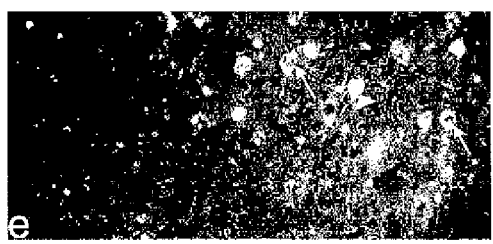
Figure 3F:
Figure 3G:

As shown in FIG. 3, in one embodiment, double labeled neurons, with both HM and fast blue labeling, are found only in the light treated group (FIGS. 3d, e, f) and the percentage of these neurons represented a statistically significant increase in comparison to the control group (FIG. 3d, $p<0.05$, Mann-Whitney U Test). This increase in double labeling indicates that only CST axons in the light treated group regrew and terminated in the gray matter of vertebral level L3 after transaction.

Figure 13:
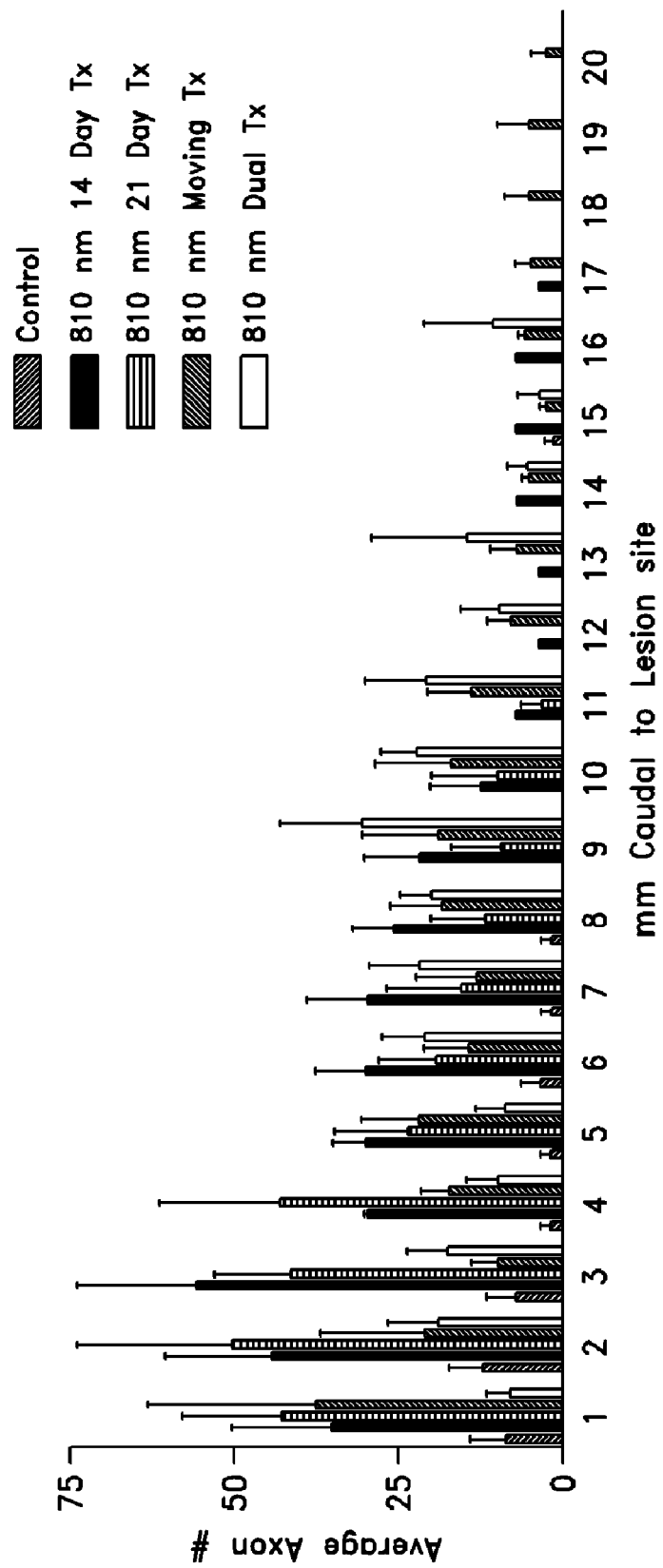
FIG. 13. Axonal growth. Average axonal number caudal to the lesion site was determined at 3 weeks post-injury following assignment to 14 day, 21 day, dual treatment with 14 day lesion site and days 11-15 motor cortex treatment, 7 day lesion site followed by 7 days of 1 mm/day caudal movement of the treatment zone, and control groups. Error bars represent the average axonal number +/−SEM.

In another embodiment of the invention, injured rat spinal cords were evaluated after LT of the lesion site for three weeks, two weeks with irradiation of the motor cortex, and one week followed by 1 mm/day movement of the irradiation zone caudal to the lesion site. Axonal regeneration was assessed using mini-ruby retrograde tract tracing as previously described. No differences were found between treatment regimens for the number of axons identified at a given distance (FIG. 14), but statistically significant differences were found in axon length in the dual treatment and moving treatment groups (FIG. 13).

Growth factor production was also assessed three weeks post-injury. Significant increases in vascular endothelial growth factor (VEGF) production was found in the tissue of the two week treatment group at both the lesion site and 10 mm caudal to the lesion site. No change was noted the production of neurotrophin-3 (NT3) and brain-derived neurotrophic factor (BDNF).

Figure 4A:
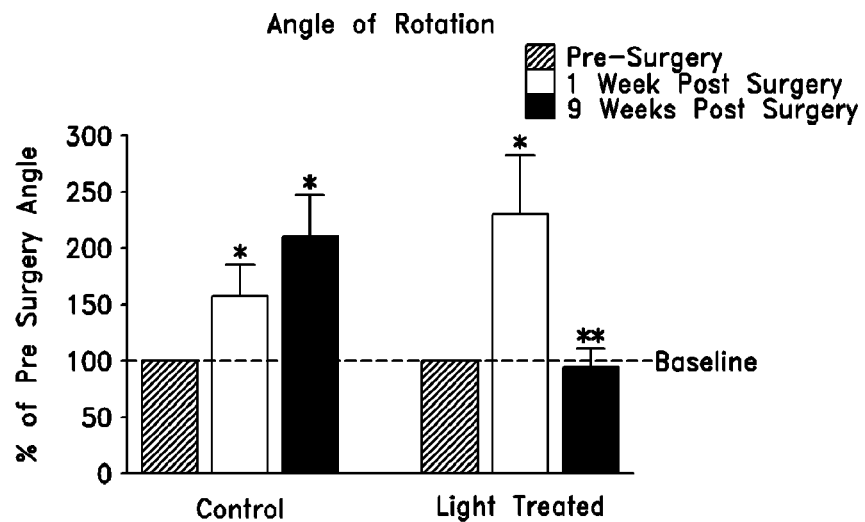
FIG. 4. Angle of rotation (a), footfalls (b) and ladder beam crossing time (c) measurements are presented for pre-surgical, 1 week and 9 weeks postsurgical time points. Significant improvement was found only in the light treated group. Graph bars are mean percentage of pre-surgical measurements +/−SEM. *$p<0.05$ using repeated measures ANOVA with Newman Keuls post-test between time points. **$p<0.05$ using one way ANOVA with Tukey post-test between control and light treatment group at 9 week time point. d) Footprints from pre-surgical and 9 weeks post-surgical analysis. Notice the increased angle of rotation and smearing at 9 weeks in the control group. In the light treated group, the angle is similar to pre-surgical values and there is no smearing of the footprint.
Figure 4B:
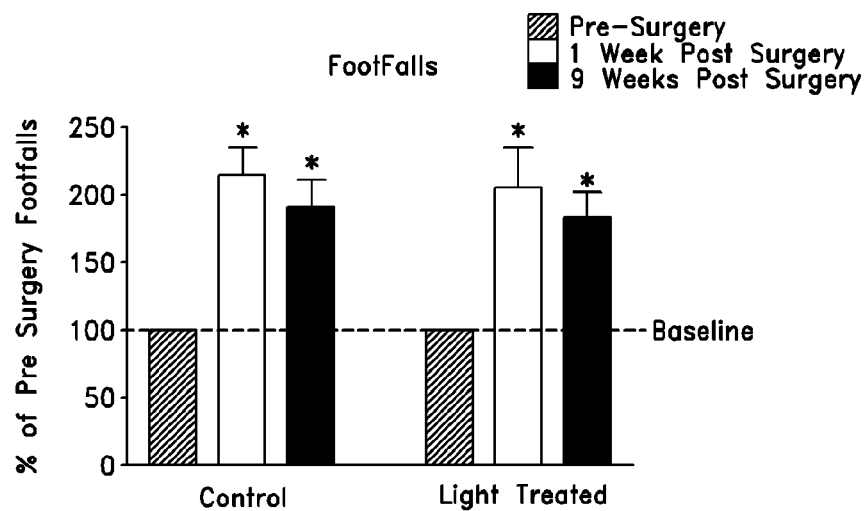
Figure 4C:
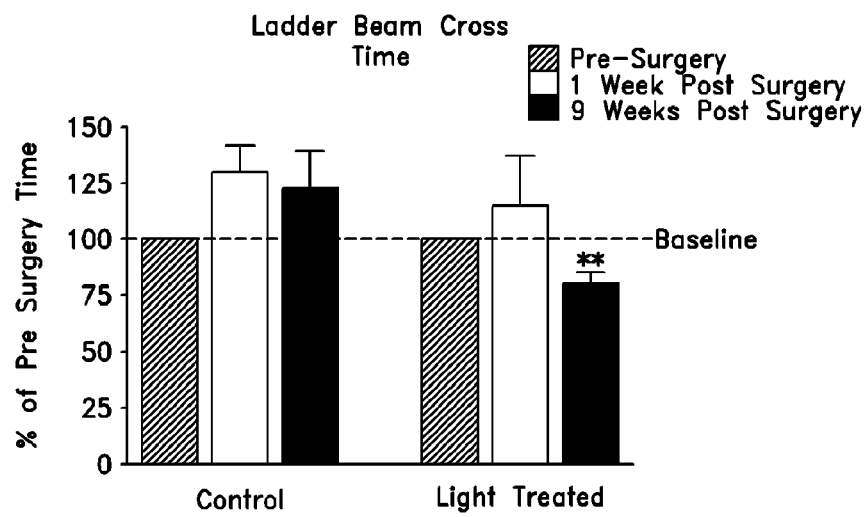

In yet another preferred embodiment, the axonal regeneration and reinnervation are evaluated by two functional tests, the ladder/grid walking test and footprint analysis, preformed prior to and after CST lesion. The measurements taken include footfalls (failure of handpass to grasp ladder rungs and falling below the plane of the ladder), time to cross the ladder, base of support, stride length, and angle of rotation. As shown in FIG. 4, in one embodiment, one week after CST lesion, experimental rats had significant impairments in angle of rotation ($p<0.05$, FIG. 4a, repeated measures ANOVA with Newman-Keuls post-test) and footfalls ($p<p\ 0.05$, FIG. 4b) in comparison to pre-surgical measurements in both control and light treated groups. An increase in ladder cross time was also observed in both groups at this time point (FIG. 4c).

Figure 4D:
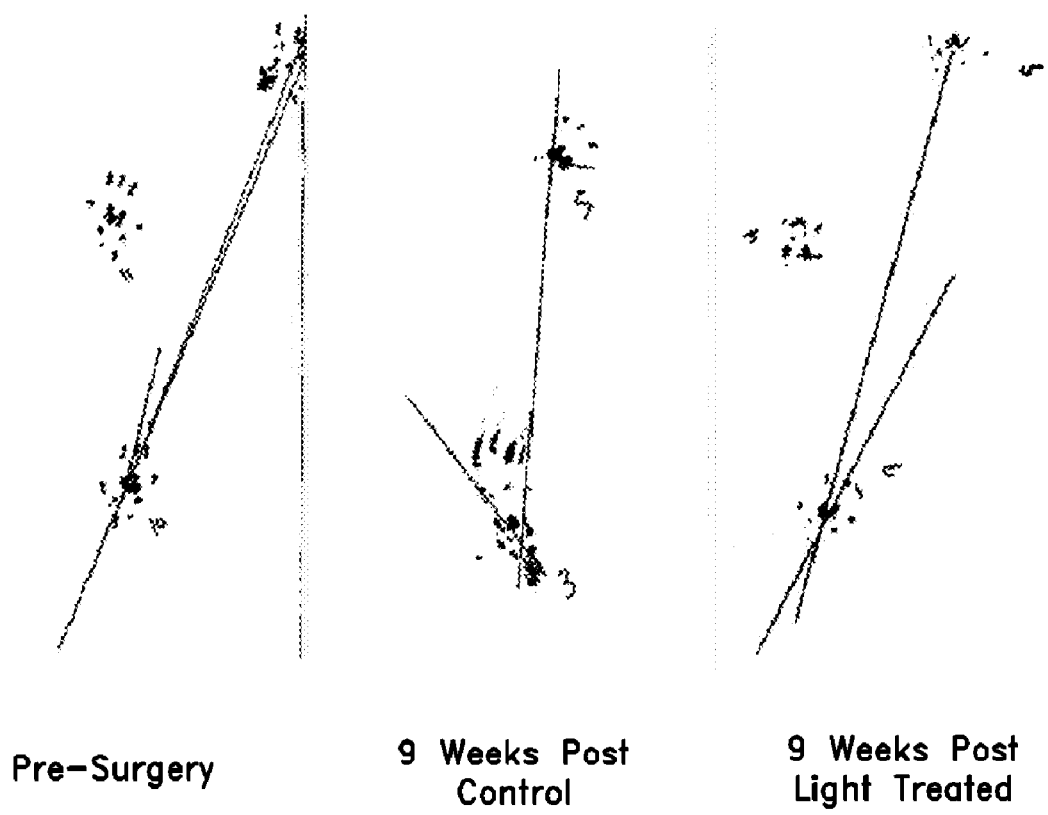

At 9 weeks post-injury, animals in the light treated group had no significant difference ($p>0.45$; FIGS. 4a, c) in angle of rotation ($p>0.05$; FIG. 4d) and ladder beam cross time in comparison to the pre-surgical measurements, demonstrating a recovery of these functions. Comparison of these measurements in the light treated and control groups revealed a significant improvement in the light treated group ($P<0.05$, FIGS. 4a, c). Comparison of ladder beam cross time and angle of rotation measurements in light treated and control groups also revealed a significant improvement in the light treated group ($p<0.05$, one way ANOVA with Tukey post-test; FIG. 4a, c). Measurements for rats that received CST lesions but were not light treated remained at the 1 week post-surgery levels at this time point, were significantly greater than pre-surgical measurements ($p<0.05$).

These measurements suggest that LT promotes significant improvement in specific CST controlled functions after lesioning, and demonstrate particular improvement in functions mediated by innervation from the L1-L3 vertebral level. Although in some cases the percentage of injured neurons that regrow is small, studies have shown that functional improvement can be found with very small amounts of axonal regrowth. [Kalderon & Fuks, *Proc. Natl. Acad. Sci. USA*, 93:11179-84 (1996), Nash et al., *J. Neurosci.*, 22:7111-20 (2002), Kalderon & Fuks, *Proc. Natl. Acad. Sci. USA*, 93:11185-90 (1996), Bregman, *Functional Neural transplantation.*, eds. Dunnett & Björklund (Raven Press, New York, pp. 489-529 (1993)), The examples described above and in further detail below confirm the observable functional improvements seen.

In yet another embodiment, the effectiveness of the LPLI treatment is evaluated by cell invasion and activation. In one embodiment, the dorsal halves of spinal cords are lesioned in adult rats and transcutaneously irradiated for a maximum of 14 days, beginning immediately after surgery, using a 150 mW 810 mn laser (1589 J/cm$^2$). The response of macrophages/activated microglia, neutrophils, T and B lymphocytes, astrocytes and Schwann cells to SCI and LPLI is quantified by immunohistochemistry at 2, 4, 14 and 16 days and 5 weeks post-injury. As shown in FIGS. 5-8, LPLI suppresses invasion/activation of macrophages and microglia as well as T lymphocytes.

Macrophage and microglia response was measured using ED1, an antibody against a macrophage/microglial lysosomal glycoprotein. Macrophages and activated microglia were not distinguished, since activated microglia express the same cellular surface molecules and have the same morphology as blood borne macrophages. ED1 expression in the macrophage/activated microglia was highest at 48 hours and 14 days post-injury. The light-treated groups exhibited statistically significant reductions in ED1 expression at 48 hours and 14 days ($p<0.001$), but not at 16 days ($p>0.05$).

Astrocyte migration and activity was assessed using antibodies against glial fibrillary acidic protein (GFAP), an intermediate filament expressed primarily in astrocytes, were used to assess astrocyte function. Astrocytes are known sources of growth factors such as NGF (nerve growth factor), FGF-2 (fibroblast growth factor-2), PDGF (platlet-derived growth factor), CNTF (ciliary neutrophic factor), IGF (insulin-like growth factor)), extracellular matrix molecules (laminin, fibronectin, vitronectin) and adhesion molecules (ICAM-1 (intercellular adhesion molecule-1), NCAM (Neural cell adhesion molecule), N-cadherin). The activation of astrocytes is delayed two days by LT, with a peak in activation occurring at 4 days post-injury. Statistically significant reductions in astrocyte activity were found in the treated rats at 48 hours and 14 days ($p<0.05$). A slight, statistically significant increase in astrocyte activity was found at 16 days ($p<0.05$).

T lymphocyte activity was also evaluated using UCHL1, an antibody against the surface glycoprotein CD45. T lymphocyte activity peaked at 48 hours post-injury in both treated and control groups, with statistically significant reductions at 16 days post-injury compared to T lymphocyte activity at 48 hours. UCHL1 expression in the light-treated rats compared to control rats was significantly decreased at 14 days post-injury. ($p<0.001$).

A similar trend is found in the migration and activation of B lymphocytes and neutrophils, in which decreases are found in the light treated group, although these are not statistically significant. LPLI appeared to have no effect on Schwann cell migration into the spinal cord. Schwann cell migration was identified by antibody labeling of S100, a neuro-specific calcium binding protein. These results indicate that light alters the spinal cord environment and the immune response following SCI.

Another aspect relates to cytokine and chemokine genes as markers and therapeutical targets/agents of SCI. Cytokines and chemokines are integral in the inflammatory response of tissue to injury. Following SCI, cytokines and chemokines are upregulated and play an important role in cellular invasion/activation and secondary damage. LPLI has significant effects on the inflammatory response of cells in vitro and in various in vivo injury models. The impact of LPLI on cytokine and chemokine gene expression after SCI are evaluated. Specifically, reverse transcriptase-polymerase chain reaction (RT-PCR) is used to detect the expression of several genes, including the pro-inflammatory cytokines interleukin (IL) 1β, IL6, tumor necrosis factor α (TNFα), and granulocyte-macrophage colony-stimulating factor (GM-CSF), the chemokines macrophage inflammatory protein 1 and monocyte chemoattractant protein (MCP-1), as well as inducible nitric oxide synthase (iNOS), intercellular adhesion molecule (ICAM) and transforming growth factor β (TGFb). All genes studied are expressed after SCI in both the LPLI and control groups, however, expression of IL6, MCP-1 and iNOS were significantly suppressed in the LPLI group. In one experiment, IL6 expression is 171 fold greater in the control group than the LPLI group at 6 hours post-injury ($p<0.001$). MCP-1 and iNOS are also suppressed at 6 hours post-injury by LPLI, with 3 and 5 fold decreases ($p<0.01$), respectively. These genes are hereby designated as SCI-related genes (SRGs).

Figure 17:
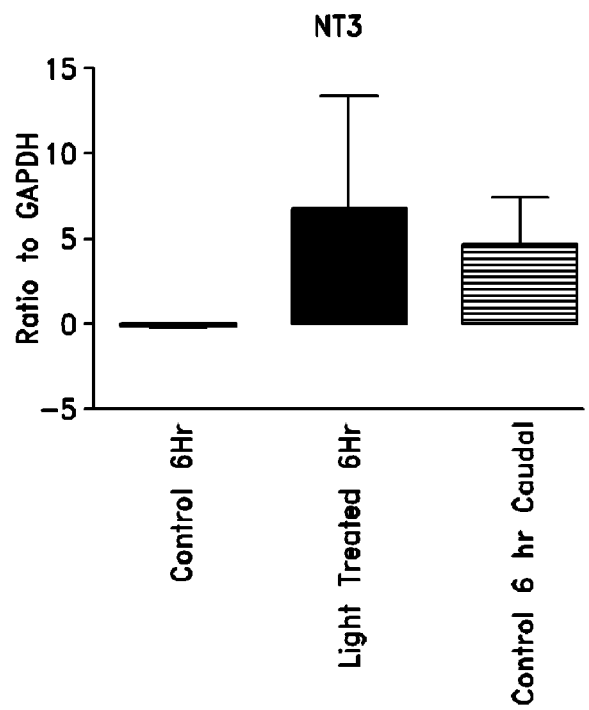
FIG. 17. NT3 (neurotrophin-3) gene expression at six hours. Expression of NT3 was assessed at six hours post-injury in the lesion site of the LT group and at a lesion site and caudal site in the control group. Error bars represent the ratio to GAPDH +/−SEM.
Figure 18:
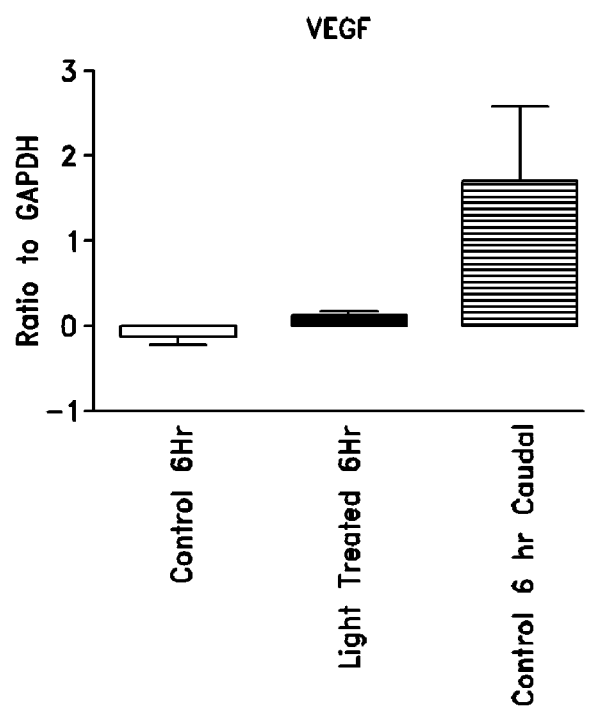
FIG. 18. VEGF gene expression at six hours. Expression of NT3 was assessed at six hours post-injury in the lesion site of the LT group and at a lesion site and caudal site in the control group. Error bars represent the ratio to GAPDH +/−SEM.

In one embodiment of the invention, RT-PCR was used to evaluate gene expression one hour post-injury. No significant differences were found in the gene expression of MCP-1 (FIG. 16, including previous study results at 6 hours and 4 days), MIP1α (mitochondrial intermediate peptidase 1a), IL1β, TNFα or IL6 at one hour. In one embodiment, RT-PCR was used to evaluate gene expression of growth factors, including NT3 (FIG. 17), VEGF (FIG. 18) and BDNF at six hours post-injury. No significant differences were found, but a trend toward was noted at longer time periods post-injury.

Therefore, without limitation as to mechanism, it appears that modulation of the expression of an SRG may ameliorate SCI when the SRG is expressed at levels similar or substantially similar to that in LPLI treated animals. Similarly, modulating the activity of an SRG product (e.g. a protein encoded by an SRG or a polynucleotide transcribed from an SRG) may ameliorate SCI when the activity of the SRG product is at levels similar or substantially similar to that in LPLI treated animals.

In one aspect, SRGs whose level of expression, which signifies their quantity or activity, is correlated with the presence of SCI. In certain preferred embodiments, one may detect the presence of an SRG product. In another aspect of the invention, the expression levels of SRGs are determined in a particular subject sample for which either diagnosis or prognosis information is desired. The level of expression of a number of SRGs simultaneously provides an expression profile, which is essentially a "fingerprint" of the presence or activity of an SRG or plurality of SRGs that is unique to the state of the cell or tissue. In certain embodiments, comparison of relative levels of expression is indicative of the severity of SCI, and as such permits diagnostic and prognostic analysis. Moreover, by comparing relative expression profiles of SRGs from tissue samples taken at different points in time, e.g., pre- and post-therapy and/or at different time points within a course of therapy, information regarding which genes are important in each of these stages is obtained. The identification of genes that are differentially expressed in SCI versus normal tissue, as well as differentially expressed genes after SCI, allows the use of the presently disclosed methods in a number of ways. For example, comparison of expression profiles of SRGs at different stages of the SCI provides a method for long-term prognosis. In another example mentioned above, the evaluation of a particular treatment regime may be evaluated, including whether a particular drug or other therapy will act to improve the long-term prognosis in a particular patient.

The discovery of these differential expression patterns for individual or panels of SRGs allows for screening of test compounds and other treatment modalities with the goal of modulating a particular expression pattern. For example, screening can be done for compounds and methods that will convert an expression profile for a poor prognosis to one for a better prognosis. In certain embodiments, this may be done by making biochips comprising sets of the significant SRGs, which can then be used in these screens. These methods can also be done on the protein level; that is protein expression levels of the SRGs can be evaluated for diagnostic and prognostic purposes or to screen test compounds. For example, in relation to these embodiments, significant SRGs may comprise SRGs which are determined to have modulated activity or expression in response to a therapy regime. Alternatively, the modulation of the activity or expression of an SRG may be correlated with the diagnosis or prognosis of SCI. In addition, the SRGs can be administered for gene therapy purposes, including the administration of antisense nucleic acids, or proteins (including dominant mutants of SRG encoded proteins, antibodies to SRG encoded proteins and other modulators of SRG encoded proteins) administered as therapeutic drugs.

In one embodiment, body fluid/tissue for the SRG screen may be obtained minimally invasively by lumbar puncture to obtain cerebrospinal fluid and/or a needle biopsy tissue sample. In another embodiment, body fluid/tissue for the SRG screen may be obtained during surgical repair of the vertebrae.

In another embodiment, a product of an SRG, either in the form of a polynucleotide or a polypeptide, can be used as a therapeutic compound of the invention. In yet other embodiments, a modulator of SRG expression or the activity of an SRG product may be used as a therapeutic compound of the invention, or may be used in combination with one or more other therapeutic compositions or methods of the invention. Administration of such a therapeutic may suppress bioactivity of an SRG product, and therefore may be used to ameliorate SCI.

EXAMPLES

Example 1

Spectrophotometric Measurement

An incoherent broad band white light was directed at the surface of the skin in the low thoracic region of five adult Sprague Dawley rats. Rats were anesthetized with sodium pentobarbital (50 mg/Kg, I.P. (intraperitoneal)) prior to all measurements. A smart, tissue-activated optical fiber probe [Ilev, I et al., *Proc Spie* 4616:220-228 (2002)] was inserted sequentially into the skin, sub-cutaneous connective tissue layer, deep connective tissue layer, muscle and the spinal cord within the vertebral column. At each of these layers, a transmission spectrum in the range of 500-1200 nm was collected while white light was applied to the skin surface.

Example 2

Corticospinal Tract Lesion

Thirty adult female Sprague Dawley rats were used in this study. For all surgical techniques, rats were anesthetized with sodium pentobarbital (50 mg/Kg, I.P.). Dorsal hemisection was performed by an investigator blinded to group assignment. The ninth thoracic vertebra was identified and a laminectomy was performed to expose the spinal cord. A suture was passed beneath the dorsal funiculus. Iridectomy scissors were used to carefully incise this isolated portion of the spinal cord, transecting the CST. Inspection of the lesion and visualization of the central gray commissure verified that the CST had been completely transected. After the hemisection was completed, the exposed spinal cord was covered with gelfoam (Pharmacia, Upjohn; Kalamazoo, Mich.), and the overlying muscles and skin were sutured. During the recovery period, urinary bladders were manually expressed until spontaneous voiding returned approximately 1-2 days post-injury.

Example 3

Retrograde Labeling

At the time of CST lesion, gelfoam soaked in hydroxystilbamidine methanesulfonate (HM; 3% in 0.9% saline; Molecular Probes, Eugene, Oreg.) was inserted into the lesion site of 20 rats. Ten weeks after the surgery, a laminectomy was performed at vertebral level L3, approximately 24 mm caudal to the original lesion site, and 1 µl of a 2% fast blue solution (in PBS, Sigma, St. Louis, Mo.) was bilaterally injected (0.5 µl into each side) into the spinal cord at a depth of 1.3 mm.

Example 4

Anterograde Labeling

Five weeks after CST lesion, 10% tetramethylrhodamine biotinylated dextran (mini-ruby, Molecular Probes) was injected into the motor cortex of one group of 10 rats (n=5 per experimental group) using stereotaxic coordinates (from bregma, −0.11 AP (anteroposterior) and ±1.60 mL (mediolateral); −1.33 AP and ±1.50 mL; −2.85 AP and ±1.40 ML; depth=1.0-1.2 mm). 2 µl of mini-ruby was injected into each of the 6 sites, for a total injection volume of 12 µl.

Example 5

Tissue Analysis for Labeling Detection

Eight days after the injections of mini-ruby or fast blue, rats were perfused with 4% paraformaldehyde. Brains and spinal cords were carefully dissected, post-fixed for 24 hours and cryoprotected in 30% sucrose for 24 hours prior to sectioning of the tissue at a thickness of 20 µm. Sections for counting mini-ruby labeled axons from the lesion site to 16 mm caudal to the lesion were collected and mounted at a ratio of 1/6. Mini-ruby labeled axons were counted at 0.5 mm intervals using a RITC (rhodamine B isothiocyanate) filter (excitation 528-553 nm) and 20× magnifications. Total axons were counted and the average number of axons per section was determined.

For neuronal counting, cortical sections were collected and mounted at a ratio of 1/8. The fractionator method of unbiased stereology was used to count HM and/or fast blue labeled neurons in the motor cortex (2.6 mm from midline to lateral edge of brain per hemisphere). The percentage of neurons that regenerated an axon was calculated according to:

$$= \frac{\text{Double labeled neurons}}{\text{Fast Blue} + HM + \text{Double labeled neurons}} \times 100$$

Cortical and spinal cord injection sites were studied prior to counting to ensure labeling efficacy; only those with adequate injections, without leakage of the tracer significant distances away from the injection site, and with adequate uptake into the intended neurons, were included in the final analysis.

Example 6

Light Treatment

Beginning immediately after transection of the CST, half of the rats (randomly assigned; n=15/group), were transcutaneously irradiated at the lesion site for a total of 14 consecutive days with an 810 nm diode laser (Thor International, UK; 150 mW output through a delivery fiber optic, 2,997 seconds treatment time/day). Dosage was 1589 J/cm² per day (irradiance=0.53 W/cm², 450 J).

Example 7

Functional Testing

One week prior, and 1 and 9 weeks after dorsal hemisection surgery, the same rats undergoing retrograde labeling were trained and then tested on two functional tests. One test required rats to walk across a ladder beam (Columbus Instruments, Columbus, Ohio) that recorded the length of time required to cross the beam as well as the number of footfalls. This test was videotaped for confirmation. Rats also underwent footprint analysis: handpass were dipped in ink and the rats walked across sheets of white paper. Base of support, stride length and angle of rotation were analyzed as described previously [Kunkel-Bagden, E et al., *Exp Neurol* 119:153-164 (1993); Hamada Y, et al., *J Neurochem* 66:1525-1531 (1996)].

Example 8

Statistical Analysis

Functional test data are presented as mean percentage of baseline scores recorded one week prior to surgery +/−SEM. Neuronal counts are presented as mean percentage of total neuronal number counted +/−SEM. Axonal counts are presented as mean +/− SEM. Functional data were analyzed using Repeated Measures ANOVA with Newman-Keuls post-test to assess changes over time or one-way ANOVA with Tukey post-test to assess differences between groups at individual time points. Axonal count data were analyzed using One Way ANOVA, with Tukey posttest. Neuronal count data were analyzed using Mann-Whitney U analysis.

Example 9

Spectrophotometric Analysis LPLI

A series of experiments involving in vivo spectrophotometric analysis were performed to assess whether transcutaneous application of 810 nm laser diode emission with an output power of 150 mW was able to penetrate to the depth of the spinal cord (FIG. 1a). Peak penetration through all tissue layers to the spinal cord was found between the 770 nm and 810 nm wavelengths (FIG. 1b). Six percent, or approximately 9 mW, of the initial power output penetrates to the spinal cord. These data show that 810 nm light, with an adequate amount of energy, reaches the spinal cord.

Example 10

Anterograde Tracer Analysis of Axon Regeneration after LPLI Treatment of SCI

Figure 2A:
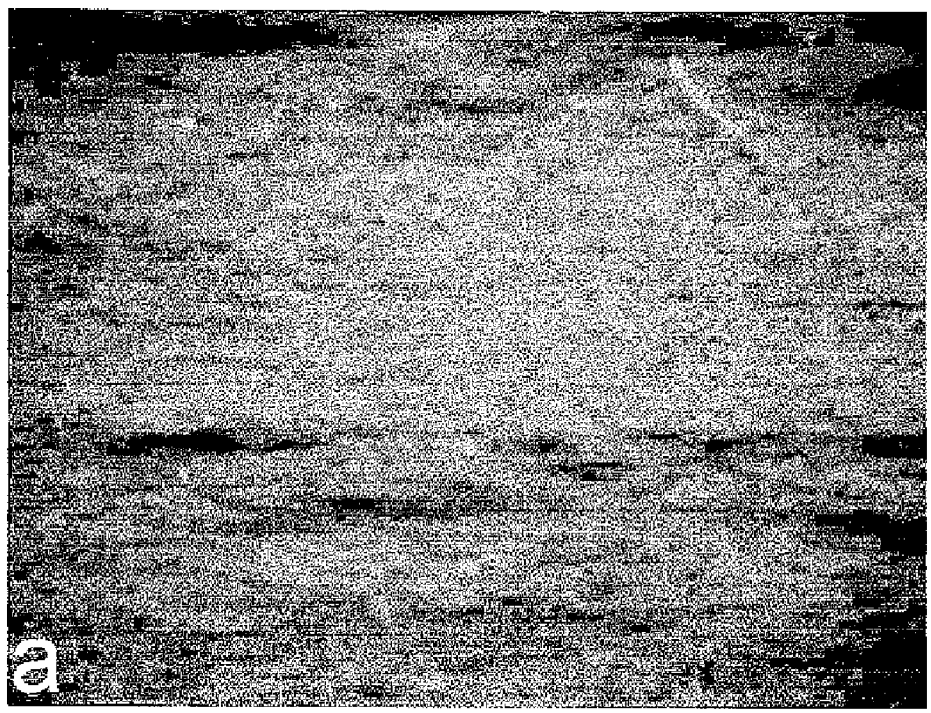
FIG. 2. Photomicrographs of mini-ruby labeled axons and related quantitation. a) Photomicrograph of white matter 4 mm caudal to lesion site in control rat. b) Photomicrograph of white matter 4 mm caudal to lesion in light treated rat. Note that mini-ruby labeled axons, indicated with arrows, are found at this distance only in the light treated group. Bar=43 μm. Comparisons of average axon number/animal (c) and average distance caudal to the lesion (d) are shown. $p<0.01$; **$p<0.001$ using one way ANOVA (analysis of variance). e) Number of axons counted in control and light treated groups per mm caudal to the lesion. Bars represent mean +/−SEM (standard error or the mean).
Figure 2B:
Figure 2C:
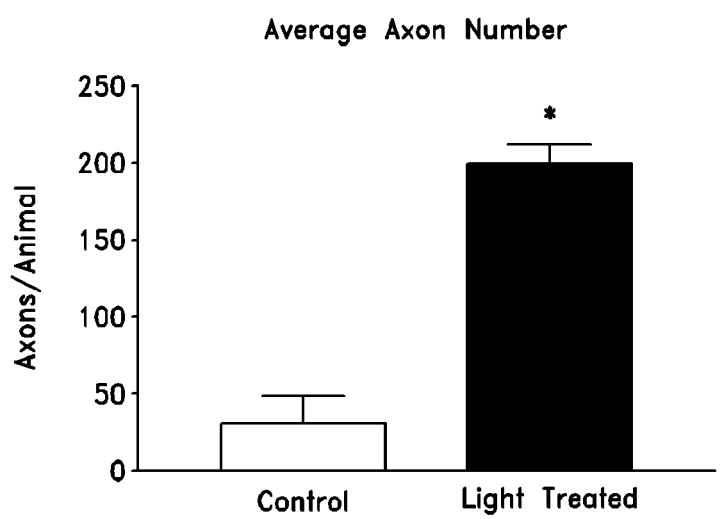
Figure 2D:
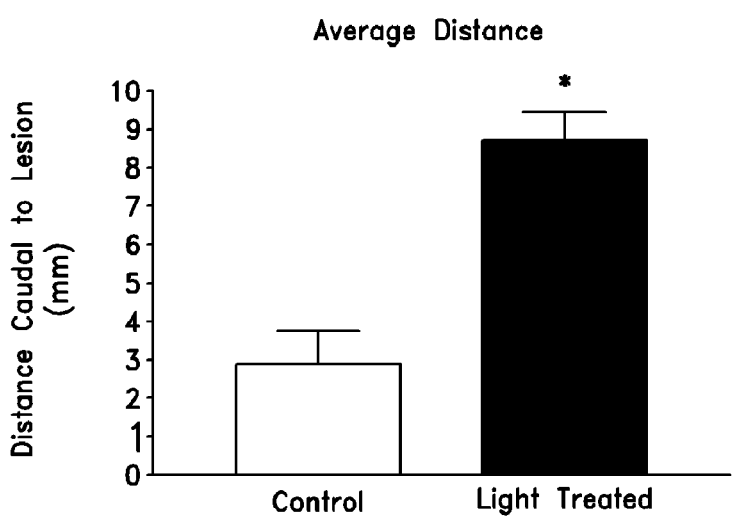
Figure 2E:
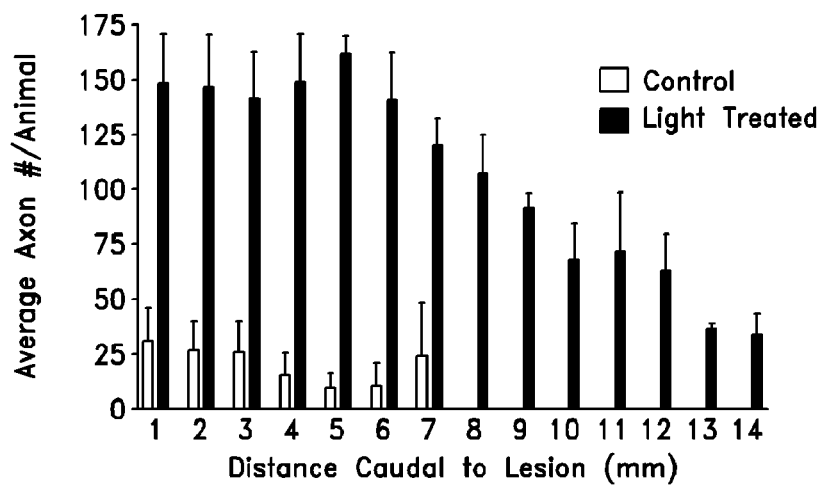

To determine if application of 810 nm light to the spinal cord increased axonal growth, Ln anterograde tracer, mini-ruby (Molecular Probes, Eugene, Oreg.), was injected 5 weeks after CST lesion. Analysis revealed that all mini-ruby labeled axons were found in the white matter, in the region of the spinal cord normally occupied by the CST (FIGS. 2a, b). There were few (30.72+/−16.9 axons per animal) mini-ruby labeled axons caudal to the lesion in the control group (FIG. 2c). These labeled axons extended an average distance of 2.9+/−0.84 mm caudal to the lesion (FIG. 2d), with a maximal distance of 7 mm reached by 17% of counted axons (FIG. 2e), which is comparable to spontaneous post-lesional sprouting previously reported [Li et al., *Neurosci.*, 61:133-139 (1994)]. The average number of mini-ruby labeled axons in the light treated group was significantly greater than that of the control group (p<0.0001, one way ANOVA with Tukey post-test; FIG. 2a), with an average of 199.2+/−12.46 labeled axons caudal to the lesion. The mini-ruby labeled axons in the light treated group extended an average of 8.7+/−0.75 mm caudal to the lesion, significantly longer than the control group (p<0.01, one way ANOVA with Tukey post-test; FIG. 2b). The maximum distance traveled over 5 weeks in the light treated group was 14 mm caudal to the lesion, which was reached by 8% of the counted axons (FIG. 2e).

Example 11

Double-label Analysis of Axon Regeneration after LPLI Treatment of SCI

Anterograde analysis does not definitively determine whether transected axons have regrown past the lesion, as spared axons may also be counted caudal to the lesion. Therefore, to determine if LPLI promotes regeneration of transected axons, a double label, retrograde tracing analysis was performed. Based on the mini-ruby data, axons in the light treated group grew at a rate of 0.25-0.4 mm per day. Using this data, we calculated that axons would likely need at least 10 weeks in order to reach the mid-lumbar region and innervate motor neurons responsible for lower limb function. At the time of CST lesion, transected neurons were labeled by an anterograde tracer, hydroxystilbamidine methanesulfonate (HM), inserted into the lesion. Ten weeks after CST lesion, axons terminating at vertebral level L3, approximately 24 mm caudal to the initial lesion, were labeled by injection of fast blue into the ventral horn. Numbers of single (HM or fast blue) and double (neurons with axons that were transected and regrew to L3) labeled neurons in the motor cortex were assessed using unbiased stereology.

Analysis of single labeled neuron number revealed no significant difference (p>0.05) between control and light treated groups, suggesting no difference in labeling efficacy between groups (FIGS. 3a, b, c). The average number of HM labeled neurons is 8,860+/−3408 in the control group and 13,270+/−3236 in the light treated group, which is comparable to the number of CST axons reported in the lower thoracic region of the spinal cord [Brosamle, C. et al., J Comp Neurol 386:293-303 (1997); Hicks, P. et al., Exp Neurol 56: 410-420 (1977)]. The average number of fast blue labeled neurons is 128.9+/108.6 in the control group and 130.9+/−119.8 in the light treated group, which is comparable to the number of neurons found in the motor cortex after injection of a retrograde tracer into the ventral, uncrossed portion of the CST at vertebral level L4 [Brosamle, C. et al., J Comp Neurol 386:293-303 (1997)]. Fast blue has been shown to spread approximately 2 mm from its injection site [Kalderon, N. et al., Proc Natl Acad Sci USA 93:11179-11184 (1996)], therefore neurons in laminae IH-VI, where ventral CST axons terminate; may have taken up the tracer. Since crossed and uncrossed axons of the CST originate from the same area of the motor cortex [Brosamle, C. et al., supra (1997)], it is likely that these fast blue labeled neurons are from the ventral, uncrossed CST that was not lesioned in the surgical procedure. The uncrossed CST axons, however, do not play a significant role in motor function in the rat [Whishaw, Q et al., Behav Brain Res 134:323-36 (2002)].

Double labeled neurons, with both HM and fast blue labeling, were found only in the light treated group (FIGS. 3d, e, f) and the percentage of these neurons represented a statistically significant increase in comparison to the control group (FIG. 3d, p<0.05, Mann-Whitney U Test). This increase in double labeling indicates that only CST axons in the light treated group regrew and terminated in the gray matter of vertebral level L3 after transaction.

This study revealed that double labeled neurons accounted for approximately 30% of the number of mini-ruby labeled axons observed at 5 weeks post-lesion in the light treated group. As double labeling represents neurons with axons that terminated in the L3 area, it is understandable that the total number of regenerating axons found at the T12 level at 5 weeks post-injury would be greater.

Example 12

Functional Evaluation of Axon Regeneration after LPLI Treatment of SCI

Complete lesion of the dorsal portion of the adult rat CST at vertebral level T9 results in loss of several CST controlled functions [Whishaw, Q et al., Behav Brain Res 134:323-36 (2002); Kunkel-Bagden, E et al., Exp Neurol 119:153-64 (1993)]. To determine if the axonal regeneration and reinnervation resulted in functional improvement, performance of rats in two functional tests, the ladder/grid walking test and footprint analysis, was assessed prior to and after CST lesion. Five measurements were taken, including footfalls (failure of hindpaws to grasp ladder rungs and falling below the plane of the ladder), time to cross the ladder, base of support, stride length, and angle of rotation. Data are presented as mean percentage of pre-surgical measurement, to control for variations among animals.

One week after CST lesion, rats had significant impairments in angle of rotation (p<0.05, FIG. 4a, repeated measures ANOVA with Newman-Keuls post-test) and footfalls (p<0.05, FIG. 4b) in comparison to pre-surgical measurements in both control and light treated groups. An increase in ladder cross time was also observed in both groups at this time point (FIG. 4c).

At 9 weeks post-injury, rats underwent these functional tests again. At this time point, animals in the light treated group had no significant difference (p>0.05; FIG. 4a, c) in angle of rotation (FIG. 4d) and ladder beam cross time in comparison to the pre-surgical measurements, demonstrating a recovery of these functions. Comparison of ladder beam cross time and angle of rotation measurements in light treated and control groups also revealed a significant improvement in the light treated group (p<0.05, one way ANOVA with Tukey post-test; FIG. 4a, c). Measurements for rats that received CST lesions but were not light treated remained at the 1 week post-surgery levels at this time point, significantly greater than pre-surgical measurements (p<0.05).

Angle of rotation and ladder cross time are both associated with CST function and are significantly lengthened by CST lesion [Kunkel-Bagden, E et al., Exp Neurol 119:153-64 (1993); Metz, A et al., JNeurosci Methods 115:169-79 (2002)]. Ladder crossing time is positively correlated with hindlimb errors in step placement [Metz, A et al., JNeurosci Methods 115:169-79 (2002)]. We found a significant increase in footfalls in both control and light treated animals post-surgery (p<0.05, FIG. 4b), but there was no significant difference between these two groups. However, analysis of errors in ladder crossing, including correct placement of hindpaws on ladder rungs and grasping of ladder rungs, was not assessed in this study and may have been modified by light treatment, leading to the observed improvement in crossing time.

No significant change was found in stride length or in base of support in either group at any time point after CST lesion (p>0.05, data not shown). Previous studies have shown that CST lesion in adult rats does not necessarily impair these functions, as this lesion does not affect the rubrospinal or propriospinal tracts, which play a greater role in these functions than the CST [Kunkel-Bagden, E et al., *Exp Neurol* 116: 40-51 (1992); Harriers, P et al., *J. Neurotrauma* 18:187-201 (2001)].

These data suggest that LT promotes significant improvement in specific CST controlled functions after lesioning. This study demonstrated particular improvement in functions mediated by innervation from the L1-L3 vertebral level. Similar results have been found with other treatment modalities, such as transplantation of fetal tissue [Kunkel-Bagden, E et al., *Exp Neurol* 116: 40-51 (1992); Kunkel-Bagden, E. et al. *Exp Brain Res* 81:25-34 (1990)].

Example 13

Dorsal Hemisection of Spinal Cord

Twenty adult female Sprague-Dawley rats (200-300 g, Taconic Farms, Germantown, N.Y.) were used in this study under an approved Uniformed Services University Institutional Animal Care and Use Committees (IACUC) protocol. Food and water were provided ad libitum and the rats were exposed to 12-hour cycles of light and dark periods.

Rats were randomly assigned to two groups (LT group, n=10; control group, n=10). Investigators were blinded to the group assignment prior to dorsal hemisection surgery. Animals were anesthetized with sodium pentobarbital (50 mg/Kg, I.P.) and placed on an isothermal heating pad warmed to 37° C. The ninth thoracic vertebra was identified and a laminectomy was performed to expose the spinal cord between T8 and T10. The dorsal funiculus was isolated by passing a suture thread through the spinal cord. Iridectomy scissors were used to carefully incise this isolated portion of the spinal cord, thereby transecting the corticospinal tract. Inspection of the lesion and visualization of the central gray commissure verified that the corticospinal tract had been completely transected.

After the dorsal hemisection was completed, the exposed spinal cord was covered with gelfoam (Pharmacia, Upjohn; Kalamazoo, Mich.), and the overlying muscles and skin were sutured. During the recovery period, bladders were manually expressed until spontaneous voiding returned at approximately 1-2 days post-injury.

Example 14

Figure 5:
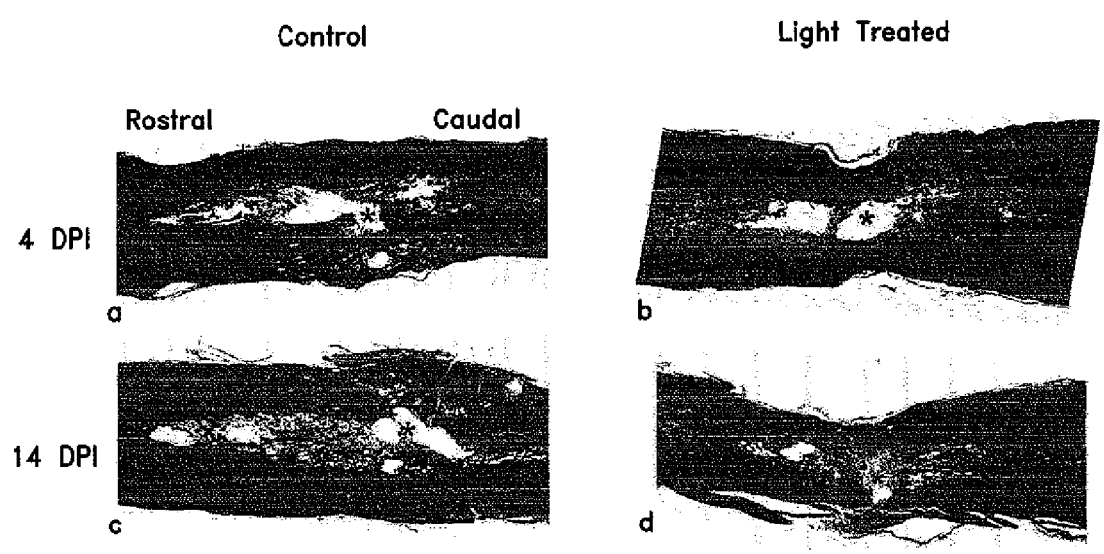
FIG. 5. Gross observation of longitudinal H&E (hematoxylin and eosin) stained sections of the thoracic spinal cord. H&E representative sections for control (a, c) and light treated (b, d) groups. Increases in cavity size were observed by 4 dpi (days post injury) in both groups (a, b) compared to 48 hours post-injury. By 14 dpi, spread of cavitation away from the center of the lesion (*) was greater in the control group (c) than the light treated group (d), particularly in the rostral direction. Cavitation was more prominent in the white matter (w) than in the gray matter (g). All tissue is oriented in the same rostral/caudal direction. Bar=250 mm.

Gross Observation of Longitudinal H&E Stained Section of the Thoracic Spinal Cord Assessment of temporal invasion/activation of the various cell types of interest was investigated within the lesion site and the surrounding tissue. Gross observation of longitudinal H&E stained sections of the thoracic spinal cord revealed a cavity at the location of the initial injury (FIG. 5). Between 48 hours and 4 dpi the size of this cavity increased (FIGS. 5a, b) and expanded longitudinally from 4 to 16 dpi (FIGS. 5a-d). This expansion extended a greater distance (1-2 mm) in the rostral direction than the caudal direction (0-0.5 mm). The cavitation spread was found primarily in the white matter of the spinal cord. The cavitation, both in the initial injury site and rostral/caudal to it, appeared to be decreased at the 5 weeks post-injury time point (data not shown). No observable difference in cavity size was seen between the control and light treated groups, however there appeared to be a decrease in longitudinal spread of the rostral cavitation in the 14 dpi light treated tissue (FIG. 5d).

Due to the clustering behavior of cells within and surrounding the lesion following spinal cord injury, and the inability to discern individual cell nuclei, assessment of numbers of individual cells was not possible. Therefore, measurement of tissue area occupied by immuno-positive label within a defined target space was used to assess cell invasion/activation. As an increase in immunolabeling does not necessarily reflect an increase in cell number, this measurement is a method of quantifying the magnitude of a cellular response, both in terms of cell invasion and activation. The current work does not attempt to distinguish between these two cellular response parameters.

Example 15

Dorsal Hemisection Lesion of the Corticospinal Tract

In one embodiment of the invention, adult female Sprague-Dawley rats were randomly assigned to light treated (n=25) or control (n=25) groups. Dorsal hemisection was performed by an investigator blinded to group assignment. A dorsal hemisection was performed at T9 by passing a suture beneath the dorsal funiculuar and carefully incising the isolated portion of the spinal cord, transecting the corticospinal tract. The transection was confirmed by lifting the suture through the lesion. Inspection of the lesion and visualization of the central gray commissure also verified transection of the CST. LT was applied to the treated group in the same fashion as specified in Example 6.

Example 16

Analysis of Cell Invasion and Activation

Spinal cord tissue from rats was collected at 48 hours, 4, 14, and 16 days and 5 weeks post-injury. At each time point, 5 rats per treatment group were deeply anesthetized with 10% chloral hydrate (1 ml/100 g, I.P.) and euthanized via intracardiac perfusion with 4% paraformaldehyde. The thoracic spinal cord at the lesion site and 3 mm rostral and 5 mm caudal to the lesion site was dissected, post-fixed for 24 hours in 4% paraformaldehyde, and cryoprotected for 24 hours in 30% sucrose. The 10 mm spinal cord segments were sectioned longitudinally on a freezing microtome at 20 µm, from the dorsal aspect of the spinal cord through the level of the gray commissure. Sections were serially mounted onto 10 slides, with 3 sections per slide. One slide from each rat was processed for histological analysis using an H&E stain and one slide/rat was processed for each cell type under investigation. Immunolabeling was repeated for each animal to ensure labeling efficacy. Negative controls, in which primary antibody was not added during immunohistochemistry, were run for each cell type (FIG. 6i).

The tissue was rehydrated and blocked with an appropriate blocking solution. Tissue was incubated overnight with primary antibodies (Table 1) followed by incubation with an appropriate fluorescently labeled secondary antibody (Jackson Immunochemicals, West Grove, Pa.) at room temperature for 30 minutes.

The lesion site and the surrounding tissue of at least 6 sections per animal per antibody were digitally photographed using a Leica/Spot system (Version 2.2 for Windows, Diagnostic Instruments, Inc. Sterling Heights, Mich.). The proportional area of tissue occupied by immunohistochemically stained cellular profiles within a defined target area (the lesion site and surrounding tissue) was measured using the Scion Image Analysis system (www.rsb.info.nih.gov/nih-image/) as described previously [Popovich et al., Supra (1997)]. All tissue sections were coded prior to measurement to prevent bias and all image backgrounds were normalized prior to quantitation.

Statistical Analysis.

Area of spinal cord occupied by cell type is expressed as mean +/−SEM. Kruskal-Wallis statistical analysis with Dunn's post-test was used to compare means (due to large mean number of pixels and large standard errors leading to the necessity of using a non-parametric test). Tests were performed using the Graph Pad Prism Program, Version 3.02 for Windows (GraphPad Software, Inc. San Diego, Calif.) and SPSS 11.0 for Windows (SPSS., Inc., Chicago, Ill.).

Neutrophils, macrophages/activated microglia and astrocytes were the primary cells found in the lesioned spinal cord. T lymphocytes, B lymphocytes and Schwann cells were also identified. However, based on our measurement of the number of immunopositive pixels in the area surrounding the lesion, there was approximately 80% less ($p<0.0001$) immunolabeling of T and B lymphocytes and Schwann cells than macrophages/activated microglia and astrocytes.

Neutrophils

Figure 6A:
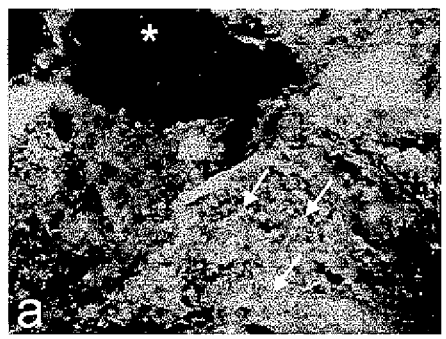
FIG. 6. Immunohistochemistry of neutrophils, macrophages and activated microglia. Immunohistochemistry for neutrophils (arrows; a, b) was found in 4 dpi tissue from both control (a) and light treated (b) groups. Quantitation of immunolabeling for neutrophils is shown in (c). Immunolabeling for macrophages/activated microglia is demonstrated in (d-h). Panel (d) is a control section from 14 dpi, demonstrating cells accumulated in and around the lesion site (*). e) Light treated tissue at 14 dpi. f) Quantitation of immunolabeling for macrophage/activated microglia. g) 16 dpi control tissue. h) 16 dpi light treated tissue. i) Negative control tissue. *$p<0.001$ between the control and light treated groups; n=5/group; ANOVA followed by Tukey test. Graph bars represent mean +/−SEM. Bar=95 mm.
Figure 6B:
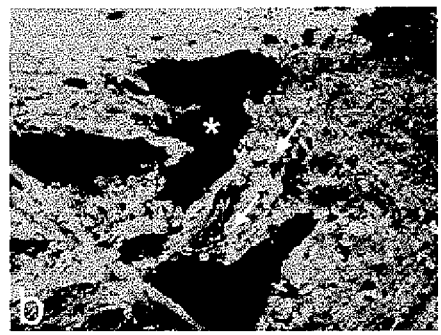
Figure 6D:
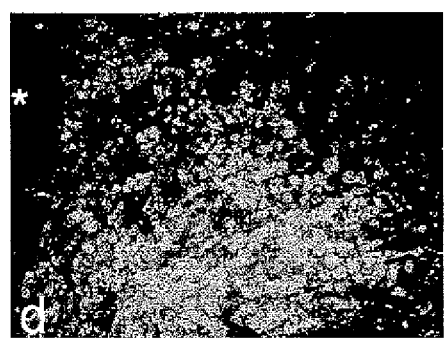
Figure 6E:
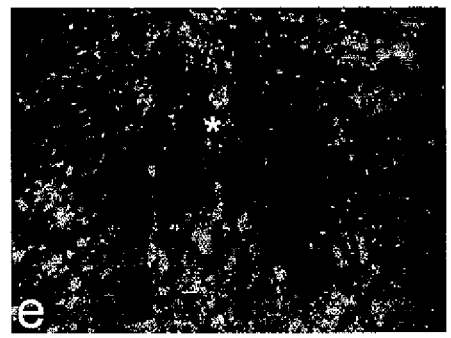
Figure 6G:
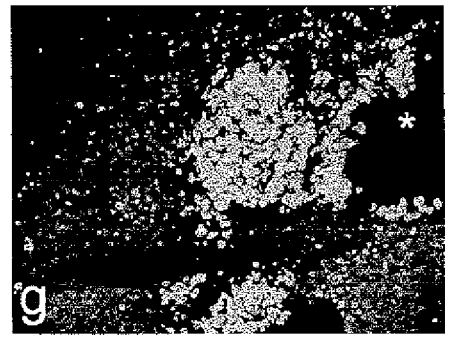
Figure 6H:
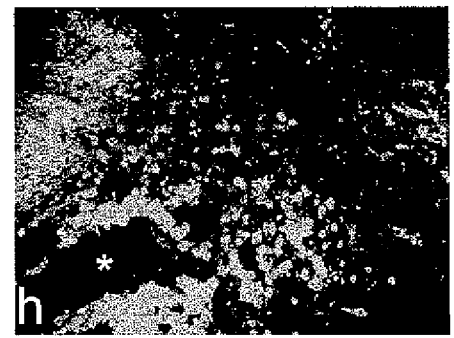
Figure 6I:
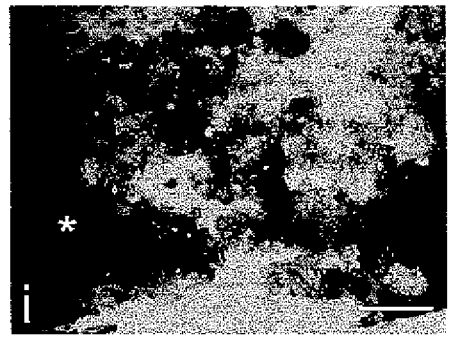
Figure 6C:
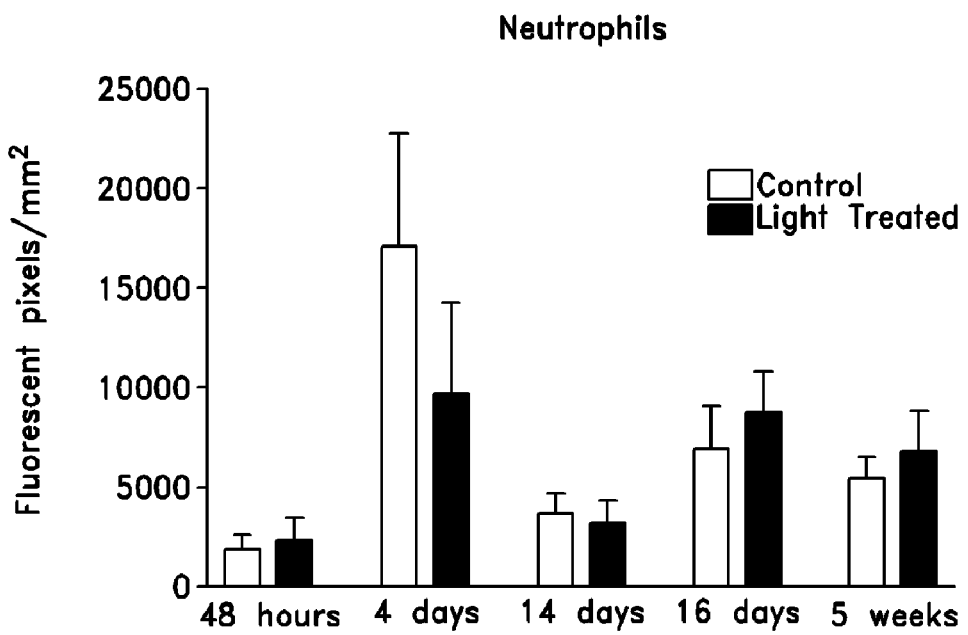
Figure 6F:
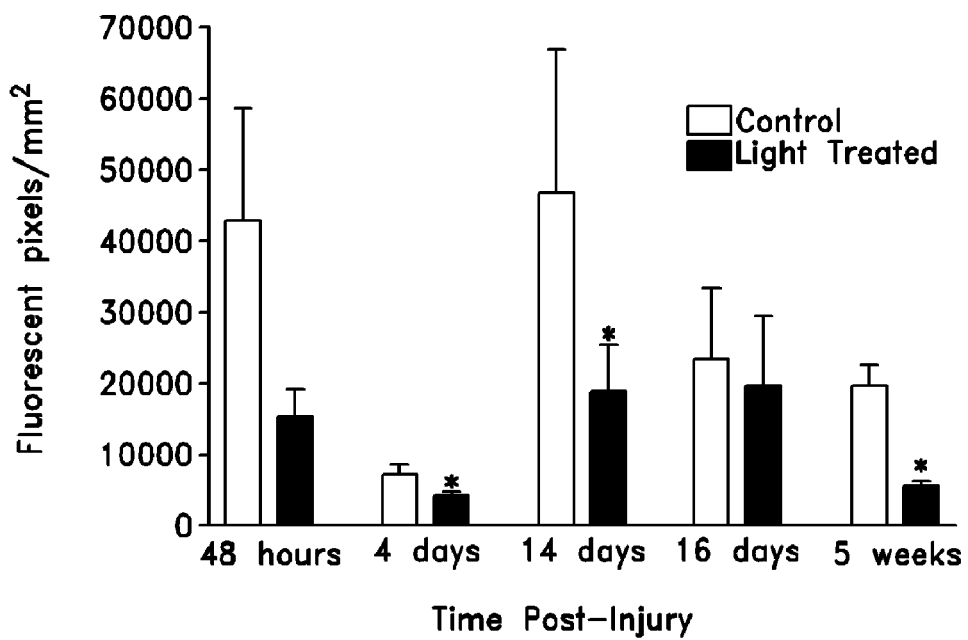

Immunohistochemical labeling with the antibody against the RP3 clone revealed small, round, cellular profiles that were detected at all time points investigated in both control and light treated groups (FIGS. 6a, b). These cells chiefly bordered the lesion site, but some cellular profiles were perivascular or adjacent to the meninges. The largest amount of positive labeling occurred at 4 dpi. This labeling was significantly increased at this time point for both light treated and control groups when compared to all other time points ($p<0.05$; FIG. 6c). However, when the amount of positive immunolabeling for neutrophils in the light treated and control tissues were analyzed, there was no significant difference at any time point (FIG. 6c). Immunolabeling for neutrophils decreased after 4 days. At 14 dpi, the remaining neutrophils in the control tissue were found not only along the edges of the lesion but also 1 mm caudal to the lesion edge. Neutrophil migration was not found in any of the light treated tissue.

Macrophages/Activated Microglia

Macrophages and activated microglia are not distinguishable from each other in the mammalian CNS since activated microglia express the same cell surface molecules and cytokines and have the same round morphology as blood borne macrophages [Popovich et al., *J. Comp Neurol* 377:443-464 (1997); Carlson et al., *Exp Neurol* 151:77-88 (1998)]. Immunolabeling for ED1, an antibody against a macrophage/microglia lysosomal glycoprotein revealed many of these large, amoeboid cells in the injured spinal cord (FIGS. 6d-h). At 48 hours post-injury, immunopositive macrophages/activated microglia were located in and around blood vessels, in the dorsal roots and along the edges of the lesion site, with no infiltration into the surrounding tissue. At this time point, there were observably fewer labeled macrophages/activated microglia in the light treated group than in the control group. By 4 dpi, a large cavity had formed and macrophages/activated microglia were localized to the lesion edges. Similar to the 48 hour situation, there were significantly fewer immunolabeled cells at 4 dpi in the light treated tissue compared to the control tissue. By 14 dpi, the immuno-positive cells were found along the edges of the lesion and within the lesion cavity (FIG. 2d), and had also invaded the tissue rostral and caudal to the lesion site, reaching up to 4 mm rostral to the lesion and 2-3 mm caudal. This cellular migration was predominantly in the white matter of the dorsal funiculus around small cavities in the rostral/caudal tissue. The light treatment group had less migration of macrophage/activated microglia at this time point (FIG. 6e), with migration reaching approximately, 1 mm in the rostral direction and absent in the caudal direction. At 16 dpi, there appeared to be fewer ED1 labeled cells in the control tissue, so that control and light treated tissue looked similar (FIGS. 6g, h).

In both control and light treated groups, ED1 expression showed an initial peak at 48 hours post-injury and a subsequent peak at 14 dpi, with a decline at 4 dpi. Both peaks were reduced in the light treated group, with significant reductions in ED1 expression at 4 and 14 dpi in the light treated group ($p<0.001$, FIG. 6f). Moreover, ED1 expression was further reduced at 5 weeks post-injury in the light treated group compared to controls ($p<0.001$, FIG. 6f). While there wasn't a significant decrease ($p=0.156$) in ED1 expression in the light treated group at 48 hours post-injury, a trend toward suppression of ED1 expression in the light treated group in comparison to the control group was found.

Astrocytes

Astrocytes were detected using an antibody against GFAP, an intermediate filament primarily expressed in astrocytes. Immunolabeling with this antibody revealed long thin processes that were heavily labeled near the lesion site in both the light treated and control groups. GFAP positive processes were also found throughout the entire length (10 mm) of the sections studied, extending 3 mm rostral and 5 mm caudal to the lesion. At 48 hours post-injury, heavy GFAP positive labeling was found to outline the lesion in all rats of the control group and GFAP positive processes were found throughout the 10 mm section in 3 of the 5 rats of the control group (FIG. 7a). Light treated tissue, however, had only a light band of GFAP positive label near the lesion edge and along the meninges/blood vessels in all 5 rats (FIG. 7b). By 4 dpi, however, GFAP labeling in the light treated tissue had increased to the degree observed in the 48 hour control tissue in 3 of the 5 rats. In both groups, immunolabeling for GFAP decreased over the remaining time periods (FIGS. 7c-f), eventually becoming restricted to the lesion site by 5 weeks post-injury. Interestingly, at 16 dpi, 2 days after light treatment ended, there was a slight increase in rostral/caudal extension of GFAP labeling in 3 of the 5 rats in the light treated group (FIG. 7f).

Quantitative analysis revealed that there was a significant decrease in GFAP expression in the light treated group at 48 hours post-injury compared to the control group ($p<0.05$), and a significant increase at 4 dpi compared to the control group (FIG. 7g, $p<0.01$). Expression peaked in the control group at 48 hours post-injury, and declined significantly ($p<0.05$) thereafter.

T Lymphocytes

Figure 8A:
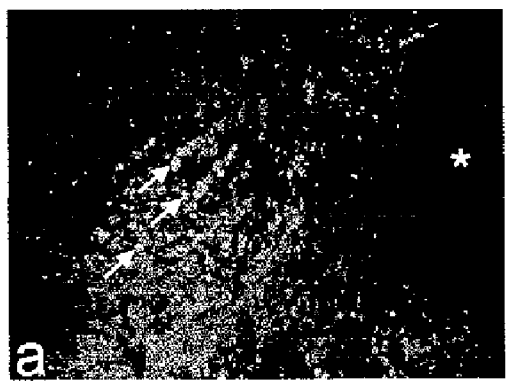
FIG. 8. Immunohistochemistry of T and B lymphocytes and Schwann cells. Images of 14 dpi tissue from control and light treated tissue are demonstrated in this figure. Immunolabeling for T lymphocytes (arrows a, b) was restricted to the lesion site (*). a) Control tissue and b) light treated tissue at 14 dpi. c) Quantitation of T lymphocyte immunolabeling. * $p<0.05$ between control and light treated tissue. d) B lymphocyte immunolabeling (arrows) in control tissue. h) Quantitation of B lymphocytes immunolabeling. Schwann cell immunolabeling (arrows) near the lesion site (*) in control (f) and light treated (g) tissue. h) Quantitation of Schwann cell immunolabeling. Graph bars represent mean +/−SEM (n=5/group; ANOVA followed by Tukey test). Bar=96 mm.
Figure 8B:
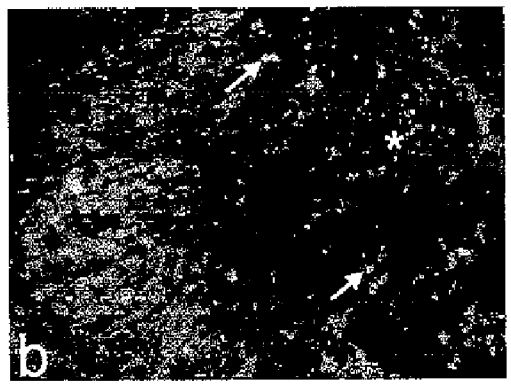
Figure 8D:
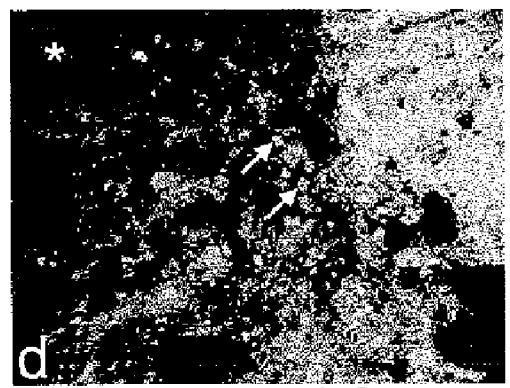
Figure 8G:
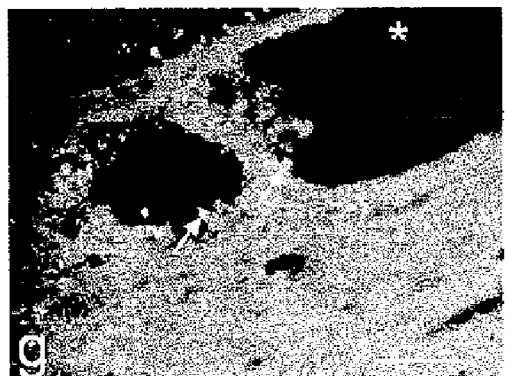
Figure 8F:

T lymphocytes were detected in spinal cord tissue using UCHL1, an antibody against the surface glycoprotein CD45. Cells that were immuno-positive for UCHLI, were small, round cells and were found in very low numbers. T lymphocytes were restricted to the lesion edge and in the acellular matrix within the lesion cavity (FIGS. 8a, b).

Figure 8C:
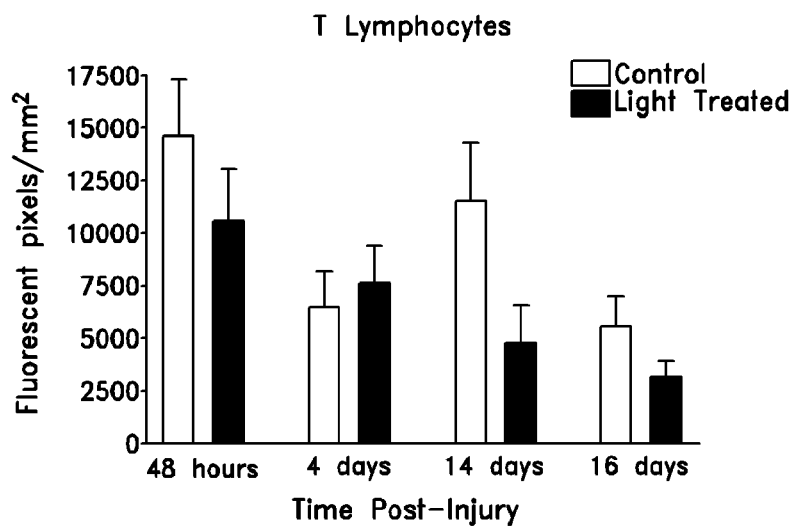

Statistical analysis of UCHL1 expression revealed that there was a peak in both the control and light treated groups at 48 hours post-injury, with a decline in expression through 16 dpi (FIG. 8c). UCHLI expression in the light treated group was lower than the control group at 48 hours, 14 and 16 dpi, with a significant decrease found at 14 dpi ($p<0.001$).

B Lymphocytes

Figure 8E:
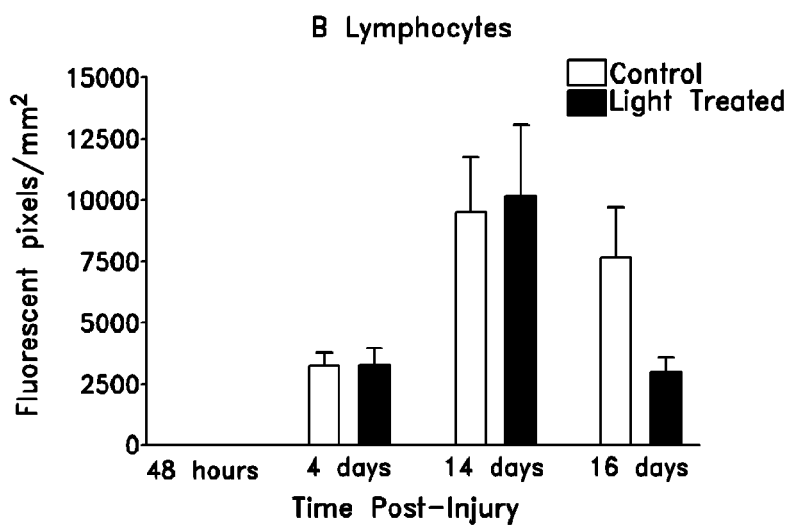

B lymphocytes, identified using the L26 antibody against CD20, a membrane spanning protein in B lymphocytes, were also found in very low numbers from 4 to 16 dpi. At the time points studied, L26 expression was found to be in small, round cells near the edges of the spinal cord lesion (FIG. 8d) or within the cavity, with 1-2 mm migration caudal to the lesion in the white matter tract at 116 dpi in the control group only. There was no migration observed in the light treated group. Quantitative analysis of L26 expression found no significant differences between the light treated and control groups, although a non-significant trend towards a suppression of B lymphocyte activation was observed in the light treated group at 16 dpi (FIG. 8e).

Schwann Cells

Figure 8H:
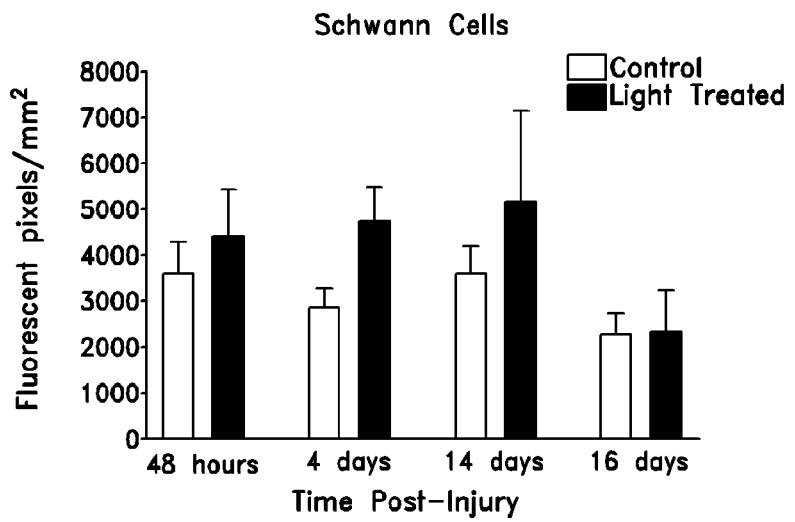

Also present in very low numbers were Schwann cells, identified by antibody labeling of S100, a neural specific $Ca^{2+}$ binding protein. These small, circular cells were found at all time points investigated, primarily along the edges of the lesion (FIGS. 8f, g), without any migration rostral or caudal to the lesion. There was no significant difference in expression between LPLI treated and control tissue at any time point (FIG. 8h).

Axons have the inherent ability to regrow following injury. Altering the spinal cord environment may support this regeneration. Transcutaneous application of light significantly affected invasion and activation of a number of cells that have a profound influence on recovery after SCI, including macrophages, microglia, astrocytes and T lymphocytes. The results of this study show that LPLI not only caused a significant inhibition of activation and invasion of several cell types, but also shifted the peak activation time in other cell types after SCI. This alteration in the temporal course of cellular reactions results in a change in the spinal cord environment at a time when axons are sprouting and entering the lesion zone (Fishman and Mattu, 1993). These results serve as a foundation for the novel concept of using transcutaneous application of light to promote axonal regeneration and functional recovery after SCI.

Example 17

RT-PCR Analysis of Gene Expression

At 6 hours or 4 days post-injury, rats (n=5/group/time point) were deeply anesthetized with chloral hydrate (1 ml/100 g, I.P., 10% solution) and euthanised by decapitation. The 5 mm of the spinal cord encompassing the lesion site and the area immediately rostral and caudal to the lesion site were dissected rapidly and placed in 500 μl of RNAlator solution (Ambion, Austin, Tex.). Total cellular RNA was extracted using the Trizol (Invitrogen, Carlsbad, Calif.)/phenol (Sigma, St. Louis, Mo.)/chloroform (Sigma) technique and reverse transcribed using First-Strand Synthesis beads (Amersham Pharmacia, Piscataway, N.J.) as per the protocol of the manufacturers (Invitrogen and Amersham Pharmacia). Resultant cDNA was amplified using the CytoXpress Multiplex Inflammatory Set 1 (Biosource, Camarillo, Calif.) or primers specific for genes of interest (Table 1). Unless otherwise noted, primer sequences were obtained with the use of the Primer3 program (Rozen and Skaletsky, 2000), with complete cDNA sequences obtained from the NIH GeneBank Entrez program. Negative (no sample added to PCR mix) and positive (provided with kit) controls were included in each PCR assay to ensure that contamination was avoided.

PCR products were assessed by electrophoresis on a 2% agarose gel containing ethidium bromide (Sigma). PCR bands were visualized using UV light and photographed. Scion Image (www.rsb.info.nih.gov/nih-image/) was used to measure band pixel density, reflecting relative gene expression. Adjustment was performed to normalize pixel intensity for samples run on different gels in order to compare the data. Pixel density for each band was obtained and normalized against the endogenous control, glyceraldehyde-3-phosphate dehydrogenase (GAPDH). All data is presented as the ratio of the gene of interest to GAPDH.

Resultant relative gene expression is presented as mean ratio +/−SEM. One-way ANOVA was used to compare groups. Tukey's Multiple Comparison test served as a post-test to the ANOVA for comparison of individual groups. All statistical analyses were performed using the GraphPad Prism Program, Version 3.02 for Windows (GraphPad Software, Inc. San Diego, Calif.).

Figure 9:
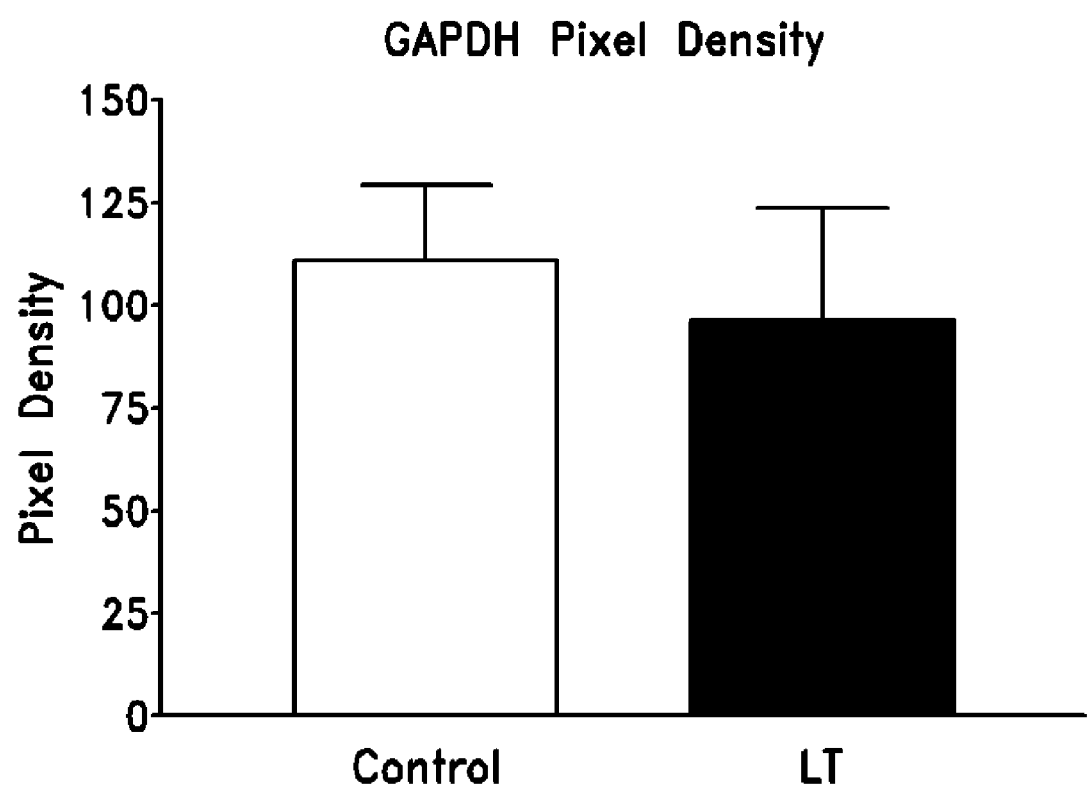
FIG. 9. GAPDH (Glyseraldehyde-3-phosphate dehydrogenase) comparison. Internal control (GAPDH) expression revealed no significant difference between the control and LT (light therapy) groups (data from 6 hours and 4 days post-injury collapsed into one group; no significant difference seen for individual time points: data not shown). $p>0.05$ (Students t-test); bars represent mean +/−SEM.

Comparison of resultant bands to the molecular weight marker confirmed that each investigated gene appeared at the expected molecular weight (data not shown). Analysis of gene expression at 6 hours and 4 days post-injury revealed that all genes were detected at all time points investigated, and no significant difference (p=0.6740) was found in expression of GAPDH between the control and LT groups (FIG. 9). Expression profiles from each sample were only included if expression for the internal control, GAPDH, could be detected. Gene expression of GAPDH for one sample of the LT-4 day group was insufficient for measurement, so this sample was not included in any data analysis. Therefore, data for this group are from four animals; all other groups were composed of five rats.

Example 18

Pro-inflammatory Cytokine Expression in LPLI Treated Animals

Figure 10E:
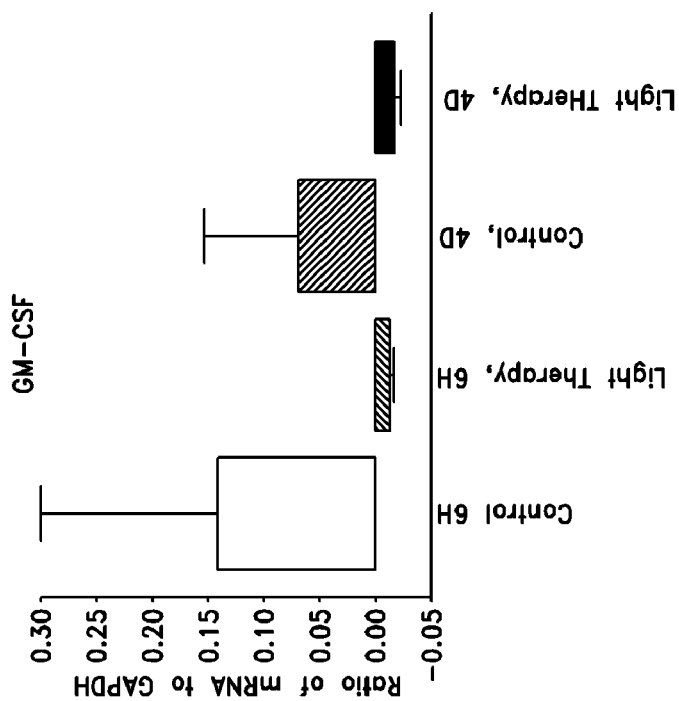
FIG. 10. Pro-inflammatory cytokine expression. Four pro-inflammatory cytokines were semi-quantitated in this study. All samples were from the site of spinal cord injury at 6 hours (H) and 4 days (D) post-injury. A) IL6 (interleukin 6) expression analysis revealed significant inhibition of IL6 mRNA production by LT at 6 hours post-injury, but no significant difference between groups at 4 days post-injury. B) Ethidium bromide-DNA complex fluorescence for IL6 from the control and LT groups, as well as their corresponding GAPDH band, at 6 hours post-injury was digitally photographed. C) IL 1b expression. D) TNFα (Tumor Necrosis Factor-α) expression. E) GM-CSF (granulocyte macrophage-conony stimulating factor) expression. *p<0001 for comparison between control and LT group at individual time point (ANOVA followed by Tukey post-test), bars represent ratio of gene of interest to internal control mean +/−SEM.
Figure 10D:
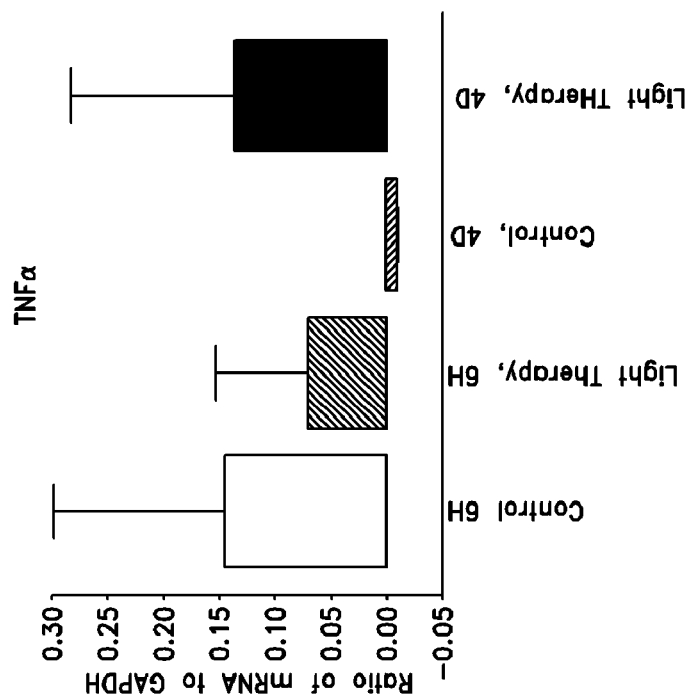

The expression of four pro-inflammatory cytokines, IL1β, TNFα, IL6 and GM-CSF, was assessed at 6 hours and 4 days post-injury. LPLI immediately following injury resulted in a significant suppression (p<0.001; FIGS. 10a, b) of IL6 expression at 6 hours post-injury. A 171-fold decrease in expression of IL6 in the LT group as compared to the control group was detected at this time point. By 4 days, transcription of IL6 had significantly decreased by 58% in the control group (p<0.001, FIG. 10a). The expression in the LT group remained depressed from 6 hours to 4 days, but there was no significant difference between IL6 levels at 4 days post-injury between the control and LT groups. There was no significant difference between control and LT groups in expression of TNFα, IL1β and GM-CSF at 6 hours post-injury or 4 days post-injury (FIGS. 10c-e). However, a trend was found in expression of GM-CSF at both 6 hours and 4 days post-injury, with a 10 and 3 fold decrease in expression found between the LT and control groups, respectively (FIG. 10e). A trend toward increase in transcription of TNFα in the LT group at 4 days post-injury was shown, although this increase was not significantly different from the control group (FIG. 10d).

Example 19

Chemokines Expression in LPLI Treated Animals

Figure 11A:
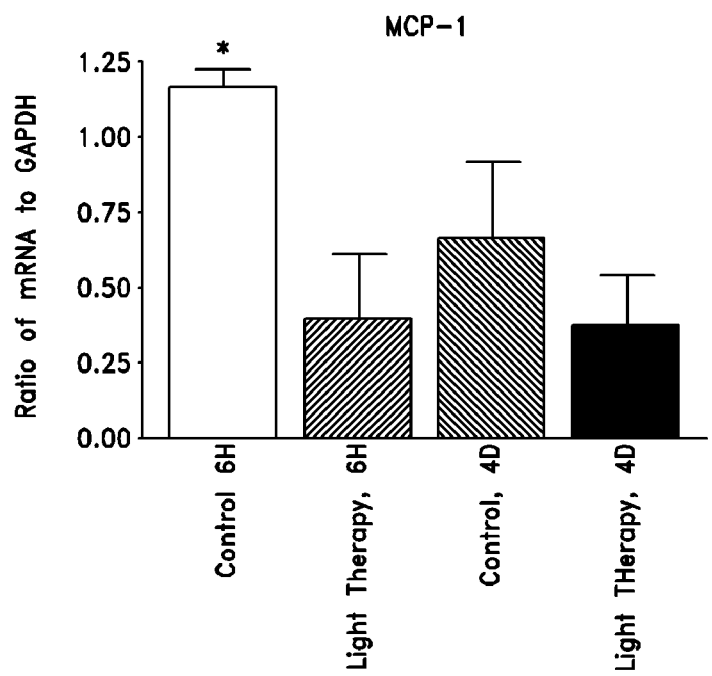
FIG. 11. Chemokine expression. Two chemokines were assessed in this study. All samples were from the site of spinal cord injury at 6 hours (H) and 4 days (D) post-injury. A) MCP-1 (Monocyte chemotactic protein-1) expression at 6 hours and 4 days after SCI. B) Representative gel bands for MCP-1 from the control and LT groups, as well as their corresponding GAPDH band. C) MIP1a (mitochondrial intermediate peptidase 1a) expression at 6 hours and 4 days after SCI. *p<0.01 for comparison between control and LT group at individual time point (ANOVA followed by Tukey post-test), bars represent ratio of gene of interest to internal control mean +/−SEM.
Figure 11B:
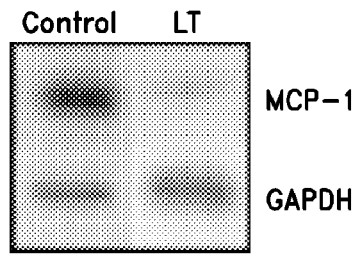
Figure 11C:
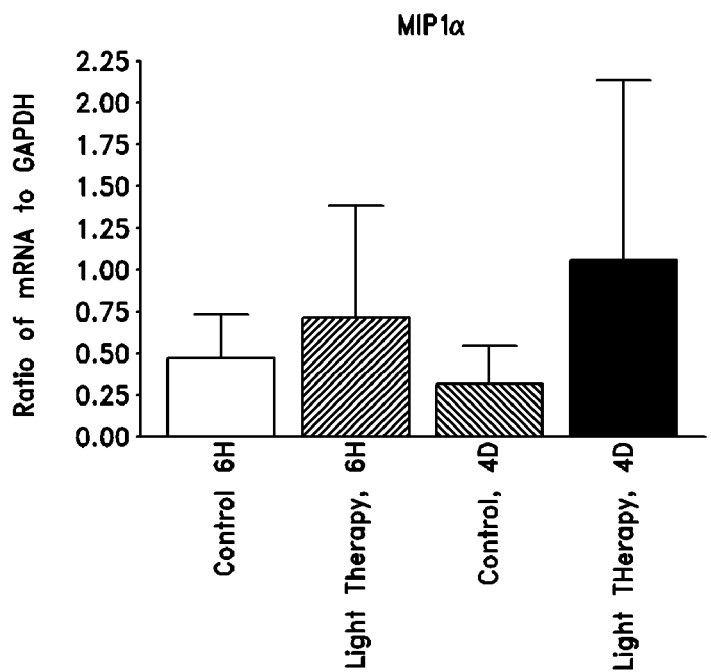

Two chemokine genes were examined in this study. Analysis of mRNA quantities for MIP1α and MCP-1 were performed at 6 hours and 4 days post-injury. Quantitation of transcription revealed that LT resulted in a significant decrease in MCP-1 at 6 hours post-injury (p<0.01, FIGS. 11a, b). The control group at this time point was found to have 66% greater expression of MCP than the LT group. This reduction in expression continued through 4 days post-injury, with a two-fold decrease in MCP-1 expression in the LT group, although this difference between the two groups' was not significant. No significant differences between the LT or control group were found at 6 hours or 4 days post-injury for MIP1α (FIG. 11c); however there was a five-fold increase in MIP1α expression at 4 days post-injury in the LT group.

Example 20

ICAM iNOS TGFβ Expression in LPLI Treated Animals

Figure 12A:
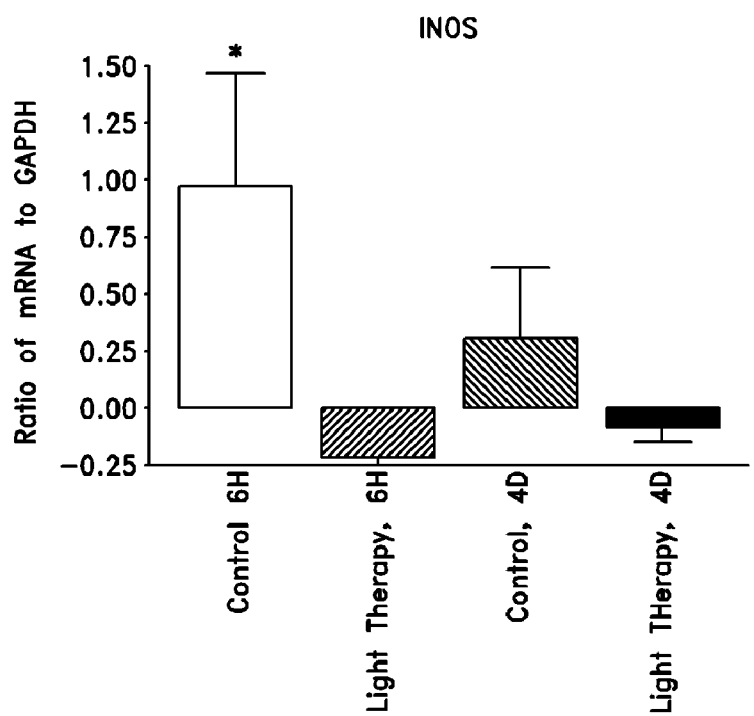
FIG. 12. iNOS (Inducible nitric oxide synthase), ICAM (Intrercellular adhesion molecules) and TGFβ (Transforming growth factor beta) expression. Expression of iNOS, ICAM and TGFβ were assessed at 6 hours (H) and 4 days (D) post-injury. A) iNOS expression at 6 hours and 4 days post-injury. B) ICAM expression. C) TGFβ expression. *p<0.01 for comparison between control and LT group at individual time point (ANOVA followed by Tukey post-test), bars represent ratio of gene of interest to internal control mean +/−SEM.
Figure 12B:
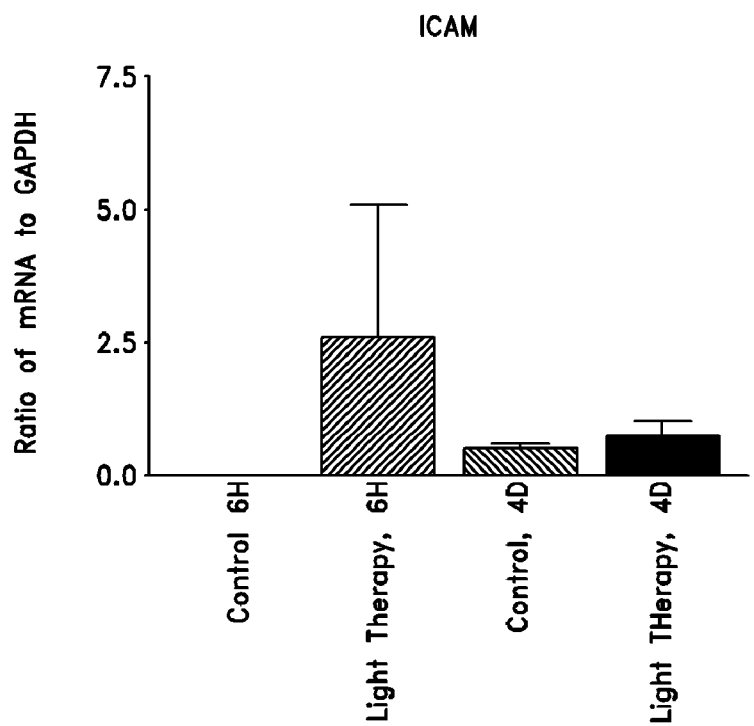
Figure 12C:
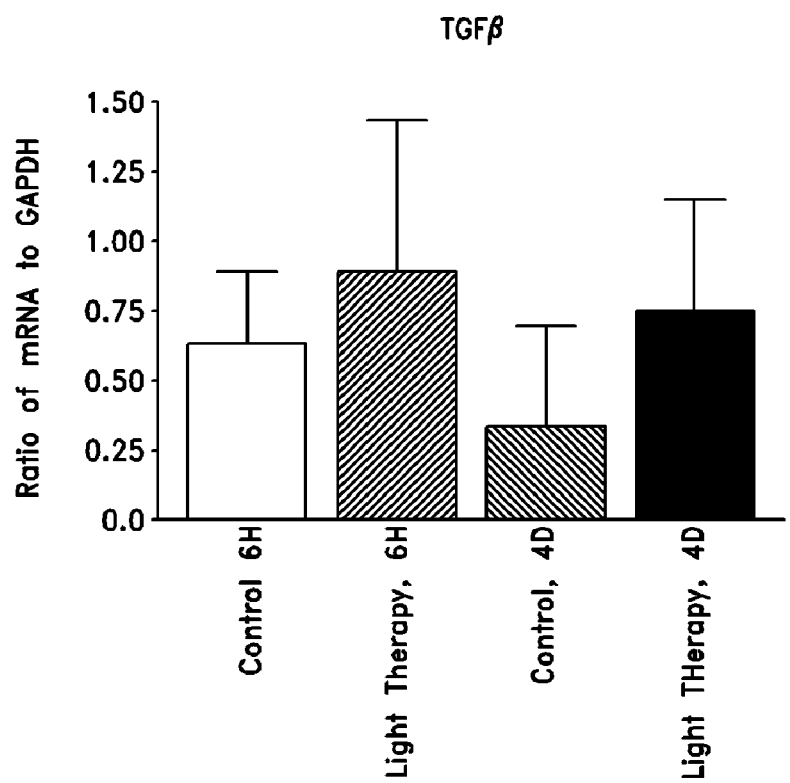

Gene expression was also evaluated for iNOS, ICAM and TGFβ. Analysis of gene expression revealed that LT resulted in a five-fold suppression of iNOS transcription at 6 hours post-injury (p<0.01; FIG. 12a), and a four-fold decrease in iNOS at 4 days post-injury that did not reach statistical significance. Again, similar to the situation with IL6 and MCP-1, iNOS expression was significantly decreased (p<0.01, FIG. 12a) in the control group from 6 hours to 4 days post-injury, but the expression levels were relatively constant over this time period in the LT group. TGFβ and ICAM, however, demonstrated a trend towards increase at both 6 hours and 4 days after injury in the LT group, although this increase did not reach statistical significance (FIGS. 12b, c).

Example 21

Alternative LT Treatment Paradigms

Figure 14:
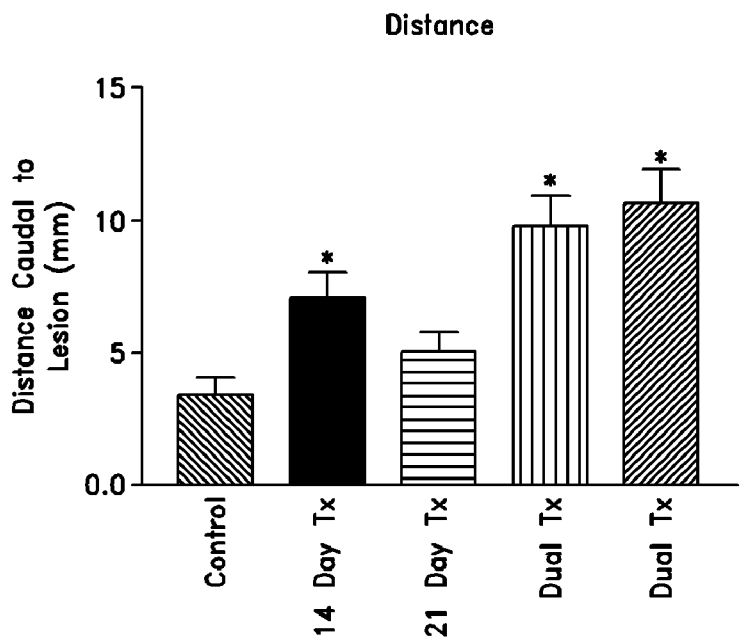
FIG. 14. Axonal distance. Regrowth distance caudal to the lesion site at three weeks was assessed using mini-ruby retrograde tract tracing in the five treatment groups in FIG. 13. Error bars represent the distance (mm) caudal to the lesion site +/−SEM.

To determine the efficacy of other treatment protocols using LT, rats were assigned to receive either: a) treatment at the lesion site for 14 days post-injury, b) treatment at the lesion site for 21 days post-injury, c) treatment at the lesion site for 14 days post-injury, with treatment of the motor cortex using 4 J/cm² dosage on days 11 to 15 post-injury (dual treatment), and d) treatment of the lesion site for 7 days post-injury followed by progressive movement of the laser 1 mm caudal to the lesion site every day for 7 days (moving treatment). Axonal regeneration was assessed three weeks post-injury using mini-ruby retrograde tract tracing as previously described. Significant increases in the distances traveled by axons were found in the dual treatment and moving treatment groups (FIG. 13). No significant differences in axonal number at any distance were found among the treatment groups (FIG. 14).

Example 22

VEGF, NT3 and BDNF Growth Factor Production in LPLI Treated Animals

Figure 15:
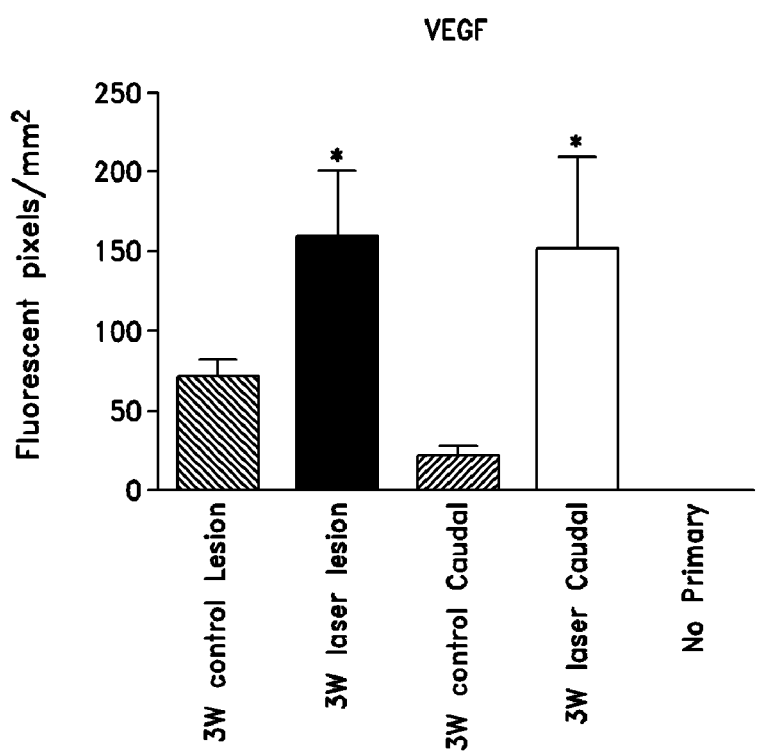
FIG. 15. Vascular endothelial growth factor (VEGF) production. VEGF production at three weeks post-injury was compared between the 14 day treatment group and control group. VEGF production was measured in spinal cord tissue at the lesion site and 10 mm caudal to the lesion site, bars representing fluorescent pixels/mm$^2$+/−SEM.

Growth factor production of vascular endothelial growth factor (VEGF), neurotrophin-3 (NT3) and brain-derived neurotrophic factor (BDNF) were also evaluated 3 weeks post-injury. A significant increase in VEGF production was found in the tissue of the 14 day treatment group at both the lesion site and 10 mm caudal to the lesion site (FIG. 15). No differences were found with other treatment paradigms or the other growth factors evaluated (NT3 and BDNF). This suggests that LT may affect the vascularization of the spinal cord following injury, which may promote axonal regeneration and functional recovery.

Example 23

Gene Expression in LPLI Treated Animals

Figure 16:
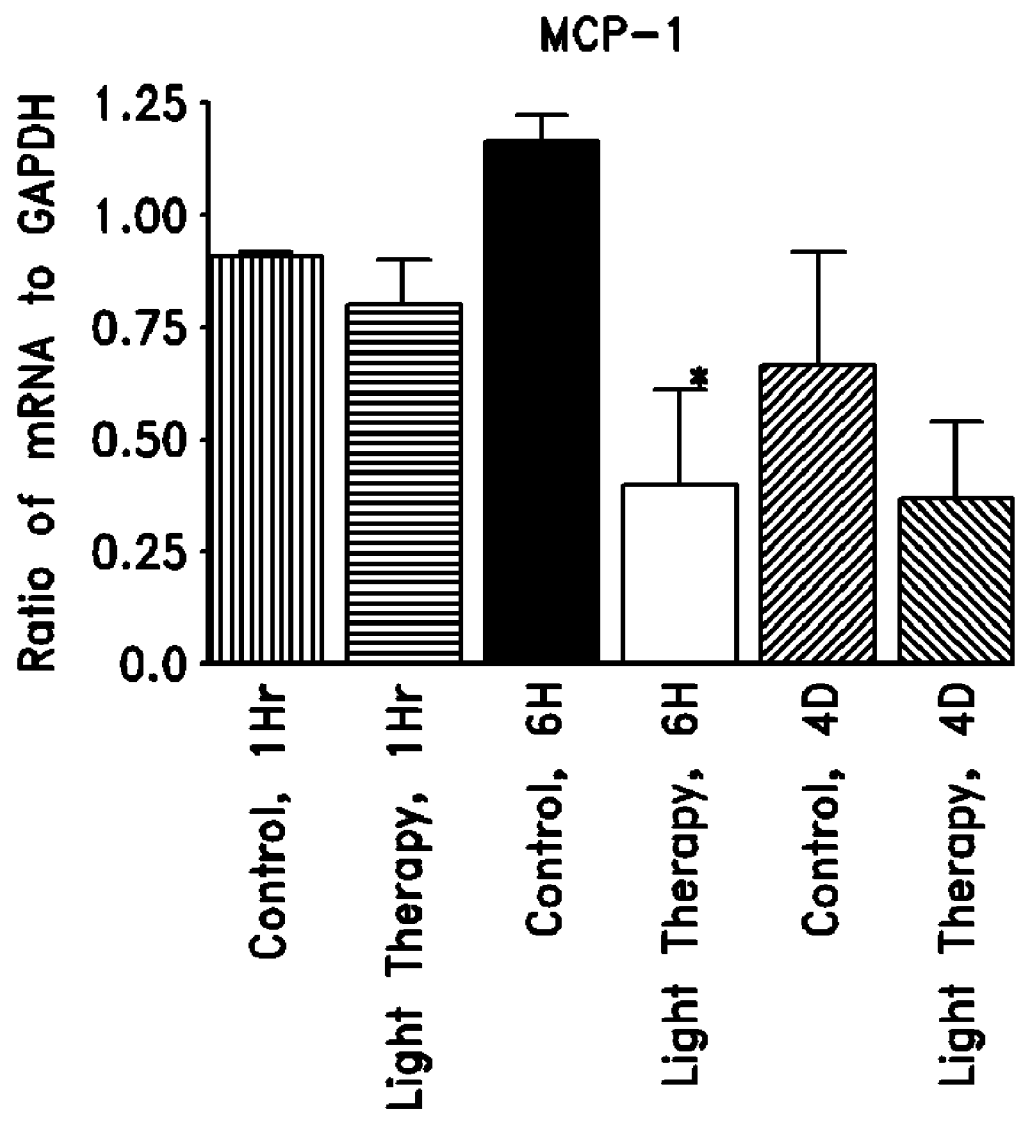
FIG. 16. MCP-1 gene expression at one hour. Expression of MCP-1 was assessed at one hour and compared to previously collected data at 6 hours and 4 days post-injury. Error bars represent the ratio of mRNA (messenger RNA) to GAPDH +/−SEM.

Gene expression of MCP-1, MIP1α, IL1β, TNFα or IL6 was also evaluated at one hour post-injury using the RT-PCR technique previously described. No significant differences were noted between the treated and control groups at one hour. FIG. 16 depicts gene expression of MCP-1 (ratio of mRNA to GAPDH) at one hour, six hours and four days post-injury. Gene expression of VEGF, BDNF and NT3 growth factors at six hours post-injury were also assessed. No significant differences were identified (FIGS. 17, 18), but a trend toward significance was noted at longer post-injury intervals. These outcomes suggest that LT may affect growth factor expression after injury and thus promote axonal regeneration.

Although the examples provided above suggest possible mechanisms by which LT may promote axonal preservation, axonal regeneration and/or functional recovery of the spinal cord, use of LT to treat SCI patients is not limited to the mechanisms provided. LT may also act through other mechanisms of action, including but not limited to, modulation of vascular effects such as the breakdown of the blood-brain barrier, cytotoxic swelling, hemorrage, neovascularization, neuronal effects on Wallerian degeneration, Schwannosis and/or demyelination, and effects on neuronal calcium concentrations, ATP production, generally cellular activity and metabolism, changes to cellular transcription themselves, or a combination of factors. In addition to direct effects on the spinal cord tissue, LT may also affect the cerebrospinal fluid, meningeal tissue, and spinal cord vasculature. The mechanism of action may also vary, depending upon the wavelength and dosage of LT used. In one embodiment, a treatment protocol with multiple wavelength and/or dosages are used to provide a particular LT treatment.

In one embodiment, LT is preferably performed continuously throughout the treatment period. In other embodiments, LT is performed with alternating periods of irradiation and rest during the treatment period. Examples of alternating treatment protocols include but are not limited to two weeks of continuous treatment every three months, one hour per day for three months, alternating 12 hour periods of irradiation and rest, alternating 50 minutes of irradiation and 10 minutes of rest, alternating 4 seconds of irradiation and 1 second of rest, and pulsed irradiation at 2 Hz to about 20 Hz. One skilled in the art will understand that any of a variety of treatment protocols may be used with LT.

In one embodiment, multiple light sources are used to treat the spinal cord injury. In one embodiment, multiple light sources are initiated at different times during a treatment protocol. In some embodiments, the wavelengths of the multiple light sources may differ. In some embodiments the treatment field size and location may change during the treatment protocol.

In one embodiment of the invention, a neuroregenerative dosage of light therapy is delivered to a target area generally about a spinal cord injury site. In one embodiment, the neuroregenerative dosage of light therapy is capable of a power intensity of at least about 0.01 mW/cm² at the desired target site. In another embodiment, the neuroregenerative dosage of light therapy is a light therapy capable of a power intensity of at least about 0.1 mW/cm² at the skin surface overlying the target site. In one embodiment, the light source or sources are positioned about 50 cm or less from the skin surface overlying the target site of spinal cord injury. In another embodiment, the light source is positioned about 20 cm or less from the skin surface overlying the target site of spinal cord injury. In still another embodiment, the light source is preferably positioned about 0.5 cm to about 2.0 cm from the skin surface overlying the target site of spinal cord injury. In another embodiment, the neuroregenerative dosage of light therapy is calculated based upon the distance between the skin surface and at least a portion of the spinal environment. The spinal environment generally includes the spinal cord, cerebrospinal fluid, meninges, spinal vasculature and adjacent structures.

While the methods disclosed herein have been particularly shown and described with references to embodiments thereof, it will be understood by those skilled in the art that various changes in form and details may be made therein without departing from the spirit of the invention. For the embodiments described above, the steps of the methods need not be performed sequentially. The above description is for the purpose of teaching the person of ordinary skill in the art how to practice the disclosed methods, and it is not intended to detail all those obvious modifications and variations of it which will become apparent to the skilled worker upon reading the description. It is intended, however, that all such obvious modifications and variations be included within the scope of this description.

What is claimed is:

1. A method of treating a patient with a spinal cord injury, the method comprising:

irradiating a first portion of a skin surface of the patient with light, the first portion of the skin surface at least partially overlying a spinal environment of the patient, the spinal environment comprising the meninges, the cerebrospinal fluid, and the spinal cord, wherein the light is directed in a direction that generally intersects at least a portion of the spinal environment; and irradiating a second portion of the skin surface of the patient with light, the second portion of the skin surface at least partially overlying at least a portion of the motor cortex of the patient's brain.

2. The method of claim 1, wherein the light irradiating the first portion of the skin surface has a power density of at least about 0.1 mW/cm$^2$ at the first portion of the skin surface.

3. The method of claim 1, wherein irradiating the first portion of the skin surface is performed for a first specified treatment period and irradiating the second portion of the skin surface is performed for a second specified treatment period.

4. The method of claim 3, wherein the first specified treatment period is two weeks, wherein the first portion of the skin surface either is irradiated continuously during the first specified treatment period or is irradiated with alternating periods of irradiation and rest during the first specified treatment period.

5. The method of claim 3, wherein the second specified treatment period is in a range between about 11 days and about 15 days after the initiation of the first specified treatment period, wherein the second portion of the skin surface either is irradiated continuously during the second specified treatment period or is irradiated with alternating periods of irradiation and rest during the second specified treatment period.

6. The method of claim 1, wherein the light irradiating the first portion of the skin surface has a wavelength in a range between about 580 nanometers and about 850 nanometers.

7. The method of claim 1, wherein the light irradiating the first portion of the skin surface has a wavelength in a range between about 720 nanometers and about 820 nanometers.

8. The method of claim 1, wherein the light irradiating the first portion of the skin surface has a wavelength of about 810 nanometers.

9. The method of claim 1, wherein the light irradiating the second portion of the skin surface has a wavelength in a range between about 580 nanometers and about 850 nanometers.

* * * * *

UNITED STATES PATENT AND TRADEMARK OFFICE
CERTIFICATE OF CORRECTION

PATENT NO.       : 7,695,504 B2
APPLICATION NO.  : 11/970425
DATED            : April 13, 2010
INVENTOR(S)      : Juanita J. Anders et al.

It is certified that error appears in the above-identified patent and that said Letters Patent is hereby corrected as shown below:

At column 5, line 5, delete "conony" and insert therefore, --colony--.

At column 5, line 25, delete "(Intrerecllular" and insert therefore, --(Intercellular--.

At column 10, line 8, delete "(platlet" and insert therefore, --(platelet--.

At column 10, line 9, delete "neutrophic" and insert therefore, --neurotrophic--.

At column 10, line 53, delete "(TGFb)." and insert therefore, --(TGFβ).--.

At column 15, line 40-41, delete "128.9+/108.6" and insert therefore, --128.9+/-108.6--.

At column 18, line 22, delete "funiculuar" and insert therefore, --funicular--.

At column 24, line 29, delete "hemorrhage," and insert therefore, --hemorrhage--.

Signed and Sealed this

Seventh Day of December, 2010

David J. Kappos
*Director of the United States Patent and Trademark Office*